US012637671B2

(12) United States Patent
Luo et al.

(10) Patent No.: US 12,637,671 B2
(45) Date of Patent: May 26, 2026

(54) GENETIC TOOLS FOR RECOMBINING TRANSGENES AT THE SAME LOCUS

(71) Applicant: The Board of Trustees of the Leland Stanford Junior University, Stanford, CA (US)

(72) Inventors: Junjie Luo, Stanford, CA (US); Mark J. Schnitzer, Stanford, CA (US); Cheng Huang, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 420 days.

(21) Appl. No.: 18/248,978

(22) PCT Filed: Oct. 15, 2021

(86) PCT No.: PCT/US2021/071904
§ 371 (c)(1),
(2) Date: Apr. 13, 2023

(87) PCT Pub. No.: WO2022/082225
PCT Pub. Date: Apr. 21, 2022

(65) Prior Publication Data
US 2023/0323342 A1 Oct. 12, 2023

Related U.S. Application Data

(60) Provisional application No. 63/092,644, filed on Oct. 16, 2020.

(51) Int. Cl.
*C12N 15/11* (2006.01)
*C12N 9/22* (2006.01)
(52) U.S. Cl.
CPC .............. *C12N 15/111* (2013.01); *C12N 9/22* (2013.01); *C12N 2310/20* (2017.05); *C12N 2800/80* (2013.01)

(58) Field of Classification Search
None
See application file for complete search history.

(56) References Cited

U.S. PATENT DOCUMENTS 7,351,578 B2     4/2008   Cheo et al.
9,689,012 B2 *   6/2017   Cunnac et al. .... C12N 15/1041

FOREIGN PATENT DOCUMENTS

WO        2012/148497 A2    11/2012

OTHER PUBLICATIONS

Beard, W. et al., "Substrate-induced DNA Polymerase β Activation," Journal of Biological Chemistry, 289(45):31411-31422, Nov. 7, 2017.
De Oliveira, M. et al., "The codA gene as a negative selection marker in Citrus," SpringerPlus, 4:264, Jun. 17, 2015, 7 pages.
International Patent Application No. PCT/US2021/071904, International Search Report and Written Opinion of the International Searching Authority, May 3, 2022, 9 pages.
Marton, T. et al., "Use of CRISPR-Cas9 to Target Homologous Recombination Limits Transformation-Induced Genomic Changes in Candida albicans," American Society for Microbiology, mSphere, 5(5):e00620-20, Sep./Oct. 2020, 15 pages.
International Patent Application No. PCT/US2021/071904, International Preliminary Report on Patentability, Apr. 27, 2023, 8 pages.

* cited by examiner

*Primary Examiner* — Kaijiang Zhang
(74) *Attorney, Agent, or Firm* — Kilpatrick Townsend & Stockton LLP

(57) ABSTRACT
Provided herein are materials and methods useful for facilitating transgene recombination. The present disclosure relates to, for example, techniques for manipulating recombination frequencies and generating organisms that contain multiple transgenic elements docking at the same locus on a single chromosome. The time consumed by the entire recombination process is proportional to the logarithm of the number of transgenes to be recombined.

20 Claims, 26 Drawing Sheets

Specification includes a Sequence Listing.

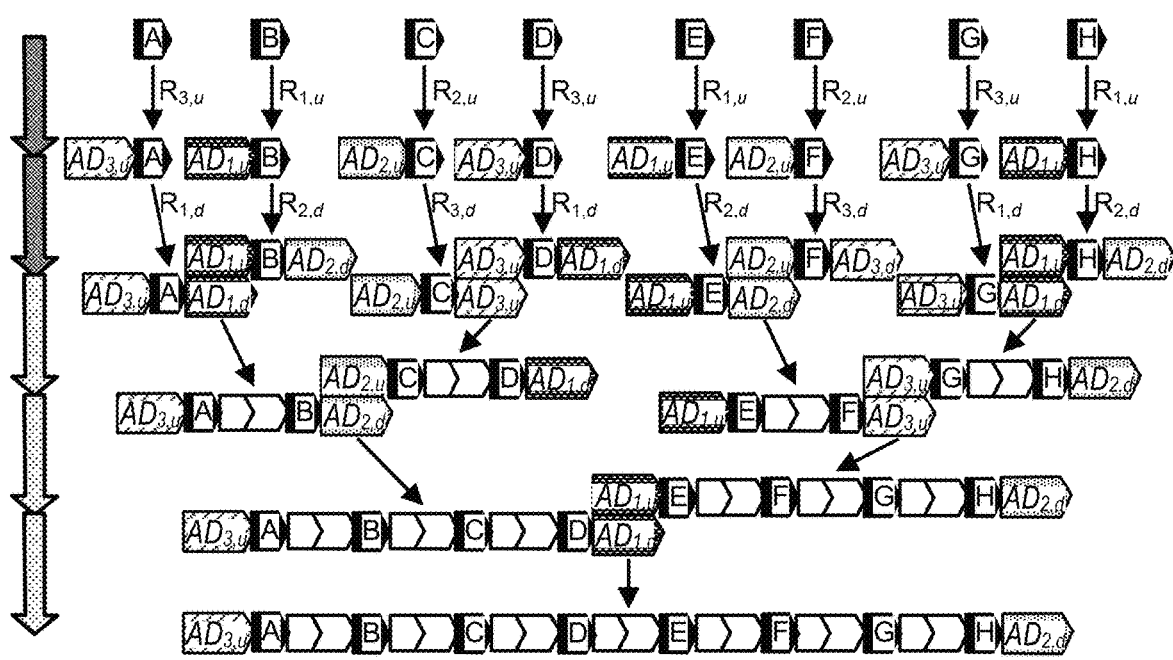
FIG. 3
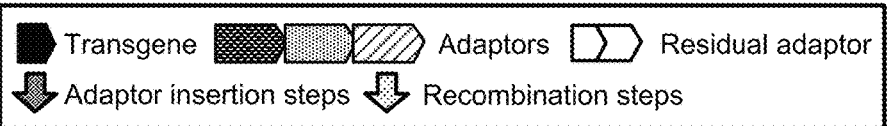
$$(l_i, l_{i+2^{\{k-1\}}}) \ X \ (l_{i+2^{\{k-1\}}}, l_{i+2^k})$$
$$\downarrow$$
$$(l_i, l_{i+2^{\{k-1\}}}) / (l_{i+2^{\{k-1\}}}, l_{i+2^k})$$
$$\downarrow X \ +/+$$
$$(l_i, l_{i+2^k}) / +, \dots$$
FIG. 4
$$l_i \neq l_{i+2^{\{k-1\}}}$$
$$l_{i+2^{\{k-1\}}} \neq l_{i+2^k}$$
$$l_i \neq l_{i+2^k}$$
FIG. 5

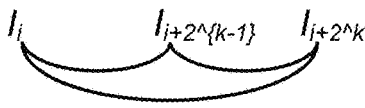
FIG. 6
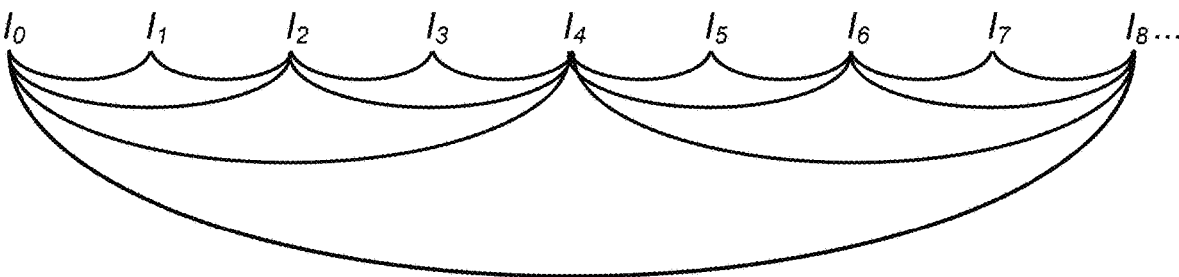
FIG. 7
$$(M_{i+1,u} \cdot M_{i+2^{\{k-1\}},d}) \times (M_{i+2^{\{k-1\}},u} \cdot M_{i+2^k,d})$$
$$\downarrow$$
$$(M_{i+1,u} \cdot M_{i+2^{\{k-1\}},d}) / (M_{i+2^{\{k-1\}},u} \cdot M_{i+2^k,d})$$
$$\downarrow \times +/+$$
$$(M_{i+1,u} \cdot M_{i+2^{\{k\}},d}) / +,$$
$$(M_{i+1,u} \cdot M_{i+2^{\{k-1\}},d}) / +, \quad (M_{i+2^{\{k-1\}},u} \cdot M_{i+2^k,d}) / +,$$
$$(M_{i+1,u} \cdot {}^*) / +, \quad ({}^*, M_{i+2^{\{k-1\}},d}) / +, \quad (M_{i+2^{\{k-1\}},u} \cdot {}^*) / +,$$
$$({}^*, M_{i+2^k,d}) / +, \quad (M_{i+2^{\{k-1\}},u} \cdot M_{i+2^{\{k-1\}},d}) / +$$
FIG. 8

$$\{M_{i+1,u}\} \cup \{M_{i+2^\wedge k,d}\} \neq \{M_{i+1,u}\} \cup \{M_{i+2^\wedge\{k-1\},d}\}$$

$$\{M_{i+1,u}\} \cup \{M_{i+2^\wedge k,d}\} \neq \{M_{i+2^\wedge\{k-1\}+1,u}\} \cup \{M_{i+2^\wedge k,d}\}$$

$$\{M_{i+1,u}\} \cup \{M_{i+2^\wedge k,d}\} \neq \{M_{i+1,u}\}$$

$$\{M_{i+1,u}\} \cup \{M_{i+2^\wedge k,d}\} \neq \{M_{i+2^\wedge\{k-1\},d}\}$$

$$\{M_{i+1,u}\} \cup \{M_{i+2^\wedge k,d}\} \neq \{M_{i+2^\wedge\{k-1\}+1,u}\}$$

$$\{M_{i+1,u}\} \cup \{M_{i+2^\wedge k,d}\} \neq \{M_{i+2^\wedge k,d}\}$$

$$\{M_{i+1,u}\} \cup \{M_{i+2^\wedge k,d}\} \neq \{M_{i+2^\wedge\{k-1\}+1,u}\} \cup \{M_{i+2^\wedge\{k-1\},d}\}$$

FIG. 9

$$M_{i+2^\wedge k,d} \neq M_{i+2^\wedge\{k-1\},d}$$

$$M_{i+1,u} \neq M_{i+2^\wedge\{k-1\}+1,u}$$

$$M_{i+1,u} \neq M_{i+2^\wedge k,d}$$

$$(M_{i+1,u} \neq M_{i+2^\wedge\{k-1\},d} \text{ or } M_{i+2^\wedge k,d} \neq M_{i+2^\wedge\{k-1\}+1,u})$$

FIG. 10

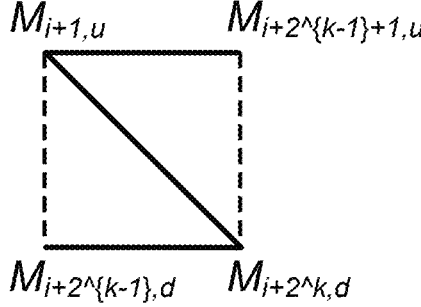

FIG. 11

FIG. 12

TG: transgene (R82C10-LexA);
AD1: Adaptor1; AD2: Adaptor2

$N_{R-,G-}/N_{total}$
***: $P < 10^{-6}$

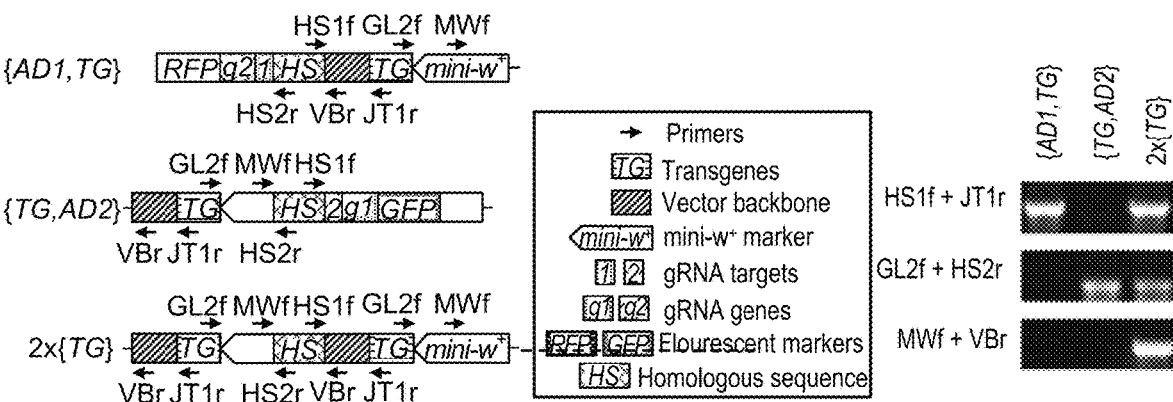
FIG. 16
{AD1,TG}...TTCCTGCAGCCCGGTCCTTCAGGTCGCCTCCGGTGGAATTGATCGGCTAA... (SEQ ID NO: 3)
{AD1*,TG}...TTCCTGCALCgaaLTCCT-----------------GGAATTGATCGGCTAA... (SEQ ID NO: 4)
{TG,AD2}  ...GTCTTGAACTCCACCGTGGACCGCTCGTCTTCCTCCGGGCTGCAGGAATT...(SEQ ID NO: 5)
{TG,AD2*}  ...GTCTTGAACT-------------------------------------GCAGGAATT... (SEQ ID NO: 6)
FIG. 17
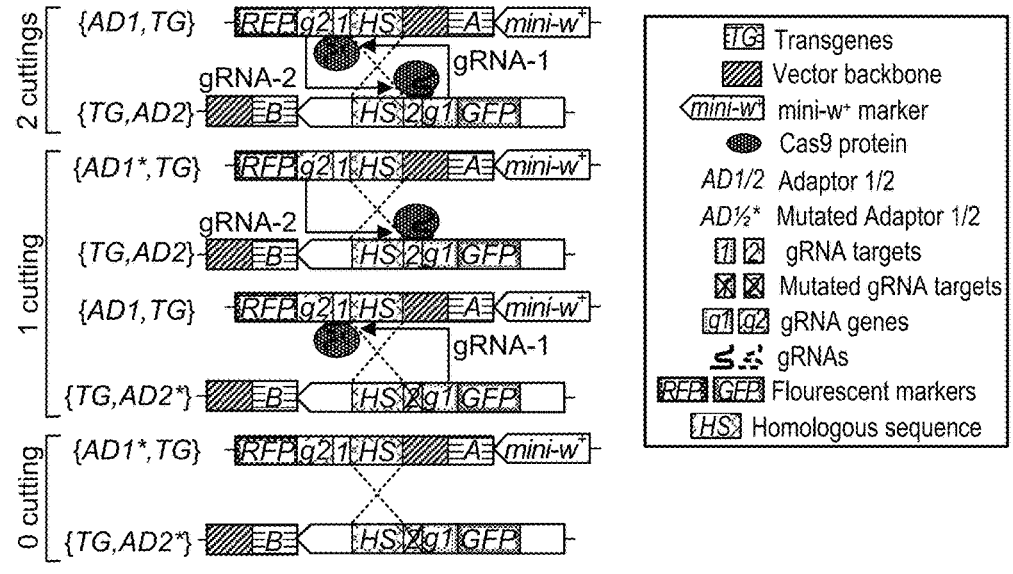
FIG. 18

TG: Transgene; AD1/2: Adaptor 1/2; AD1/2*: Mutated Adaptor 1/2

- In FIG. 27, the x-axis of the graph is missing numerical labels.

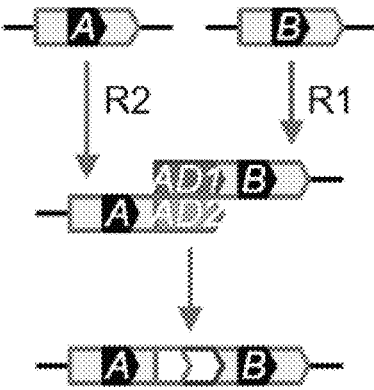
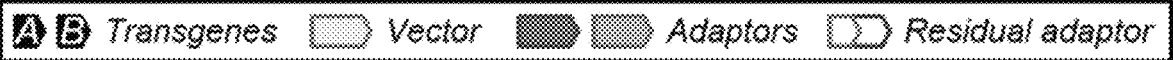
FIG. 28
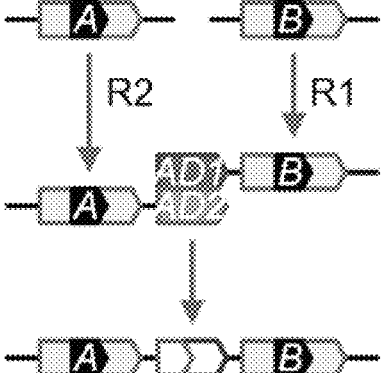
FIG. 29

$$M_{TG} X (M_1, M_{R1})$$
$$\downarrow$$
$$M_{TG} /(M_1, M_{R1})$$
$$\downarrow X \; +/+$$
$$(M_1, M_{TG})/+,$$
$$M_{TG} /+, (M_1, M_{R1})/+$$

$$M_{TG} X (M_{R2}, M_2)$$
$$\downarrow$$
$$M_{TG} /(M_{R2}, M_{R2})$$
$$\downarrow X \; +/+$$
$$(M_{TG}, M_2)/+,$$
$$M_{TG} /+, (M_{R2}, M_2)/+$$

$$\{M_{TG}\} \ U \ \{M_1\} \neq \{M_{TG}\} \qquad \{M_{TG}\} \ U \ \{M_2\} \neq \{M_{TG}\}$$

$$\{M_{TG}\} \ U \ \{M_1\} \neq \{M_1\} \ U \ \{M_{R1}\} \qquad \{M_{TG}\} \ U \ \{M_2\} \neq \{M_{R2}\} \ U \ \{M_2\}$$

FIG. 32

If $\{M_{TG}\} \neq \emptyset$:

$M_1 \neq M_{TG}, \ M_{R1} \neq M_{TG}$ $\qquad M_2 \neq M_{TG}, \ M_{R2} \neq M_{TG}$ If $\{M_{TG}\} \neq \emptyset$:

$M_1 \neq M_{R1}$ $\qquad\qquad M_2 \neq M_{R2}$

FIG. 33

$$M_{TG} \ X \ (M_{i,u}, M_{i,Ru})$$
$$\downarrow$$
$$M_{TG}/(M_{i,u}, M_{i,Ru})$$
$$\downarrow X \ (M_{j,Rd}, M_{j,d})$$
$$(M_{i,u}, M_{TG})/(M_{j,Rd}, M_{j,d}),$$
$$M_{TG}/(M_{j,Rd}, M_{j,d}),$$
$$(M_{i,u}, M_{i,Ru})/(M_{j,Rd}, M_{j,d})$$
$$\downarrow X +/+$$
$$(M_{i,u}, M_{TG}, M_{j,d})/+,$$
$$(M_{i,u}, M_{TG})/+,$$
$$(M_{j,Rd}, M_{j,d})/+$$

FIG. 34

$$\{M_{i,u}\} \cup \{M_{TG}\} \cup \{M_{j,Rd}\} \cup \{M_{j,d}\} \neq \{M_{TG}\} \cup \{M_{j,Rd}\} \cup \{M_{j,d}\}$$
$$\{M_{i,u}\} \cup \{M_{TG}\} \cup \{M_{j,Rd}\} \cup \{M_{j,d}\} \neq \{M_{i,u}\} \cup \{M_{i,Ru}\} \cup \{M_{j,Rd}\} \cup \{M_{j,d}\}$$

$$\{M_{i,u}\} \cup \{M_{TG}\} \cup \{M_{j,d}\} \neq \{M_{i,u}\} \cup \{M_{TG}\}$$
$$\{M_{i,u}\} \cup \{M_{TG}\} \cup \{M_{j,d}\} \neq \{M_{j,Rd}\} \cup \{M_{j,d}\}$$

FIG. 35

$If \{M_{TG}\} \neq \emptyset:$
$M_{i,u} \neq M_{j,Rd,}$
$M_{i,u} \neq M_{j,d,}$
$M_{i,u} \neq M_{TG,}$
$M_{i,Ru} \neq M_{TG,}$
$M_{j,d} \neq M_{TG}$

FIG. 36

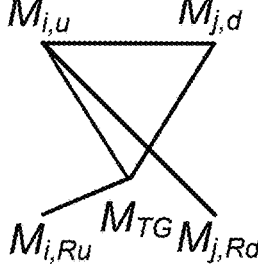

FIG. 37

$If \{M_{TG}\} \neq \emptyset:$
$M_{i,u} \neq M_{j,Rd,}$
$M_{i,u} \neq M_{j,d,}$
$M_{i,Ru} \neq M_{i,u,}$
$M_{i,Ru} \neq M_{j,Rd,}$
$M_{i,Ru} \neq M_{j,d}$

FIG. 38

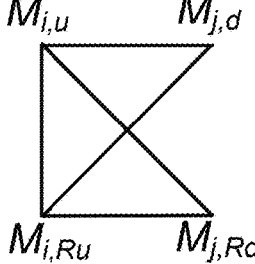

FIG. 39

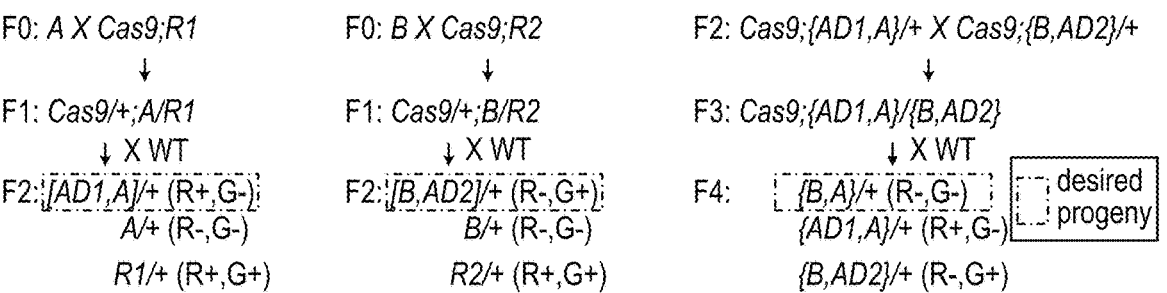
F0: *A X Cas9;R1*
↓
F1: *Cas9/+;A/R1*
↓ X WT
F2: *[AD1,A]/+ (R+,G-)*
   *A/+ (R-,G-)*
   *R1/+ (R+,G+)*
F0: *B X Cas9;R2*
↓
F1: *Cas9/+;B/R2*
↓ X WT
F2: *[B,AD2]/+ (R-,G+)*
   *B/+ (R-,G-)*
   *R2/+ (R+,G+)*
F2: *Cas9;[AD1,A]/+ X Cas9;[B,AD2]/+*
↓
F3: *Cas9;[AD1,A]/[B,AD2]*
↓ X WT
F4: *[B,A]/+ (R-,G-)*     ┌─ ─ ─┐ desired
   *[AD1,A]/+ (R+,G-)*   └─ ─ ─┘ progeny
   *[B,AD2]/+ (R-,G+)*
FIG. 53
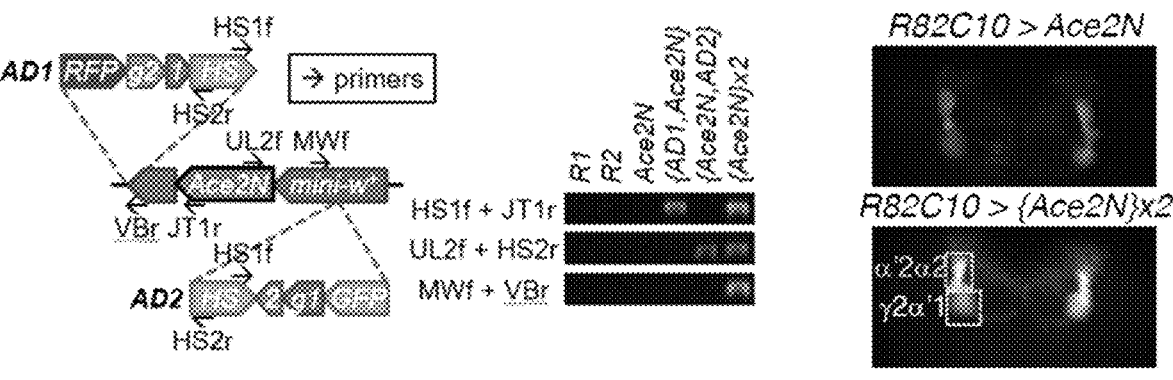
FIG. 54
FIG. 55
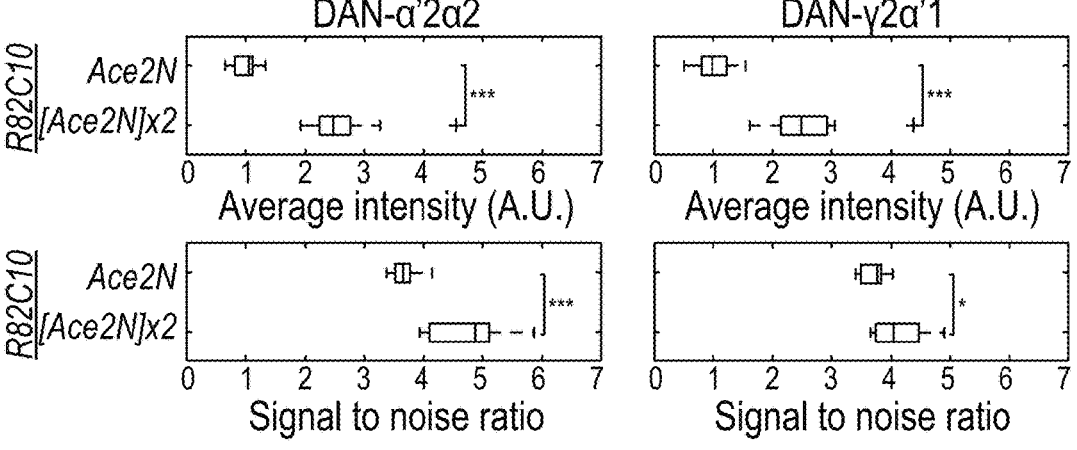
FIG. 56

SEQUENCE LISTING

<160> NUMBER OF SEQ ID NOS: 6

<210> SEQ ID NO 1
<211> LENGTH: 88
<212> TYPE: DNA
<213> ORGANISM: Artificial Sequence
<220> FEATURE:
<223> OTHER INFORMATION: The sequence is artificially synthesized

<400> SEQUENCE: 1
ttcacaaata ccatttccct aaaaataacc ttcacaaata ccatttccct aaaaataacc      60
ttcacaaata ccatttccct aaaaataa      88

<210> SEQ ID NO 2
<211> LENGTH: 158
<212> TYPE: DNA
<213> ORGANISM: Artificial Sequence
<220> FEATURE:
<223> OTHER INFORMATION: The sequence is artificially synthesized

<400> SEQUENCE: 2
ttaaaataat caggcgtaga ttaaaataat caggcggtca ttaaaataat caggcggaga      60

-continued

```
ttaaaataat caggcgatgc atttaaaata atcaggcgta gattaaaata atcaggcggt      120
cattaaaata atcaggcgga gattaaaata atcaggcg                             158

<210> SEQ ID NO 3
<211> LENGTH: 50
<212> TYPE: RNA
<213> ORGANISM: Artificial Sequence
<220> FEATURE:
<223> OTHER INFORMATION: The sequence is artificially synthesized

<400> SEQUENCE: 3
uuccugcagc ccgguccuuc aggucgccuc cgguggaauu gaucggcuaa                  50

<210> SEQ ID NO 4
<211> LENGTH: 34
<212> TYPE: RNA
<213> ORGANISM: Artificial Sequence
<220> FEATURE:
<223> OTHER INFORMATION: The sequence is artificially synthesized

<400> SEQUENCE: 4
uuccugcauc gaauuccugg aauugaucgg cuaa                                   34

<210> SEQ ID NO 5
<211> LENGTH: 50
<212> TYPE: RNA
<213> ORGANISM: Artificial Sequence
<220> FEATURE:
<223> OTHER INFORMATION: The sequence is artificially synthesized

<400> SEQUENCE: 5
gucuugaacu ccaccgugga ccgcucgucu uccuccgggc ugcaggaauu                  50

<210> SEQ ID NO 6
<211> LENGTH: 19
<212> TYPE: RNA
<213> ORGANISM: Artificial Sequence
<220> FEATURE:
<223> OTHER INFORMATION: The sequence is artificially synthesized

<400> SEQUENCE: 6
gucuugaacu gcaggaauu                                                    19
```

GENETIC TOOLS FOR RECOMBINING TRANSGENES AT THE SAME LOCUS

CROSS-REFERENCE TO RELATED APPLICATIONS

The present application is a § 371 National Stage Application of International Application PCT/US2021/071904, which claims priority to U.S. Provisional Application No. 63/092,644 filed Oct. 16, 2020, the full disclosures of which are incorporated by reference in their entirety for all purposes.

SEQUENCE LISTING

This application contains a Sequence Listing which has been submitted electronically in TXT format and is hereby incorporated by reference in its entirety. Said TXT copy, created on Mar. 18, 2026, is named 079445-006910US-1376363.txt, and is 1,934 bytes in size.

BACKGROUND

To achieve a high level of specific expression for multi-copy transgenes, or to include several reporters and effectors for complex experiments, it is desirable to create a single organism that contains multiple transgenic elements. Yet, due to the constraints imposed by genetic linkage and crossing-over and the limited number of transgene docking sites, the probability of recombining multiple transgenic elements is low. Moreover, the chance of integrating more than one transgenes at a single locus is near zero. Hence, traditional approaches for recombination are poorly suited to design organisms with a number of transgenic elements greater than the number of available docking sites.

When two genes are on different chromosomes, they assort independently. When they are on the same chromosome, the recombination frequency between them is determined by the genetic distance between the two loci. Traditional approaches to creating an organism with multiple transgenic elements involve docking these elements on different chromosomes, or integrating them at different loci far apart on the same chromosome and then recombining them. Therefore, to generate a model organism with N transgenic elements, N–1 steps of combination or recombination are required. Further, in the $k^{th}$ step, the strain containing k+1 transgenes needs to be selected from $2^{k+1}$ possible combinations in diploid organisms. The number of possible combinations is even higher in polyploidy organisms. For example, there are $4^{k+1}$ possible combinations in tetraploid organisms, and $8^{k+1}$ possible combinations in octoploid organisms.

In view of these observations and results, there is a need in the art for improved strategies for recombining transgenes at the same locus. The present disclosure addresses this need and provides associated and other advantages.

BRIEF SUMMARY

In general, provided herein are materials and methods that are particularly useful in facilitating transgene recombination. The disclosure relates to, for example, techniques for manipulating recombination frequencies and generating organisms that contain multiple transgenic elements docking at the same locus on a single chromosome. In such cases, creating an organism with N transgenic elements only requires $\log_2$ N, instead of N–1, steps of recombination, as are typically required with existing recombination procedures. Moreover, in each recombination step of the provided methods, the recombinant only needs to be selected from among a much smaller number of possible genotypes. In some embodiments, the provided techniques can be referred to as the Super Recombinator (SuRe) system. This recombination strategy also can be used to avoid difficult embryo injections, and for this and other reasons can more easily be used by a wider variety of facilities having access to only basic skills of genetic manipulation. The provided methods are suitable for making transgenic strains in organisms with sexual reproduction, including animals, plants, and some fungi. The methods can also be used in cell lines with artificially induced cell fusion.

In one aspect, the disclosure provides a method of creating a nucleotide sequence containing two or more transgenes or other nucleotide sequence fragments. The method includes providing a pair of adaptor sequences and i transgenes or other nucleotide sequence fragments, where i is an integer not less than 2. The method further includes inserting a first adaptor downstream of each transgene or other nucleotide sequence fragment x, where the first adaptor has the first sequence of the pair of adaptor sequences, and where x is an odd integer such that $1 \le x \le i-1$. The method further includes inserting a second adaptor upstream of each transgene or other nucleotide sequence fragment y, where the second adaptor has the second sequence of the pair of adaptor sequences, and where y is an even integer such that $2 \le y \le i$. The method further includes facilitating recombination between a matching linker sequence within each of the first adaptor and the second adaptor. The method further includes screening for correct recombination products using markers within each of the first adaptor and the second adaptor.

In another aspect, the disclosure provides an alternative method of creating a nucleotide sequence containing two or more transgenes or other nucleotide sequence fragments. The method includes providing 3 adaptor sequence pairs and i transgenes or other nucleotide sequence fragments, where i is an integer greater than 2. The method further includes inserting (1) a first adaptor sequence of adaptor sequence pair 1 downstream of each transgene of other nucleotide sequence fragment x, and (2) a second adaptor sequence of adaptor sequence pair 3 upstream of each transgene or other nucleotide sequence fragment x, where $1 \le x \le i$, and where x–1 is divisible by 3. The method further includes inserting (1) a first adaptor sequence of adaptor sequence pair 2 downstream of each transgene or other nucleotide sequence fragment y, and (2) a second adaptor sequence of adaptor sequence pair 1 upstream of each transgene or other nucleotide sequence fragment y, where $2 \le y \le i$, and where y–2 is divisible by 3. The method further includes inserting (1) a first adaptor sequence of adaptor sequence pair 3 downstream of each transgene or other nucleotide sequence fragment z, and (2) a second adaptor sequence of adaptor sequence pair 2 upstream of each transgene or other nucleotide sequence fragment z, where $3 \le z \le i$, and where z–3 is divisible by 3. The method further includes facilitating recombination between (1) a first matching linker sequence within each of the first adaptor sequence and the second adaptor sequence of adaptor sequence pair 1; (2) a second matching linker sequence within each of the first adaptor sequence and the second adaptor sequence of adaptor sequence pair 2; and (3) a third matching linker sequence within each of the first adaptor sequence and the second adaptor sequence of adaptor sequence pair 3. The method further includes screening for correct recombination products using markers within each of the adaptors.

BRIEF DESCRIPTION OF THE DRAWINGS

FIG. 3 is an illustration of the coordination recombination strategy. In this strategy, all adaptors are added to the transgenes in the beginning. These adaptors are coordinated to facilitate the recombination in all the following steps.

FIG. 4 is a diagram of the linker genotype in one step of recombination. A first cross is made of $(l_i, l_{i+2^{\wedge}\{k-1\}})$ with $(l_{i+2^{\wedge}\{k-1\}}, l_{i+2^{\wedge}k})$; then, the transheterozygote is crossed with a wild-type strain (or a balancer strain). In the last generation, only the genotype $(l_i, l_{i+2^{\wedge}k})/+$ is picked, with other genotypes not shown.

FIG. 5 is an expression of the orthogonality of the linker in one step of recombination. This orthogonality prevents the upstream linker of a transgenic tandem from reacting with the downstream linker of the same transgenic tandem.

FIG. 6 is a module graph representing the linker orthogonality in one step of recombination.

FIG. 7 is a graph representing the orthogonality of all linkers in the entire recombination process.

FIG. 8 is a diagram of the marker genotype in one step of recombination. A first cross is made of $(M_{i+1,u}, M_{i+2^{\wedge}\{k-1\},d})$ with $(M_{i+2^{\wedge}\{k-1\},u}, M_{i+2^{\wedge}k,d})$; then, the transheterozygote is crossed with a wild-type strain (or a balancer strain). In the last generation, only the genotype $(M_{i+1,u}, M_{i+2^{\wedge}k,d})/+$ is picked, with other undesired genotypes shown in gray.

FIG. 9 is an expression of the orthogonality of the marker in one step of recombination. The genotype $(M_{i+1,u}, M_{i+2^{\wedge}k,d})/+$ is generally distinguishable from undesired genotypes, although it is not necessary to distinguish undesired genotypes from each other.

FIG. 10 is a simplified expression of the orthogonality of the marker in one step of recombination.

FIG. 11 is a module graph representing the marker orthogonality in one step of recombination.

FIG. 12 is a simplified module graph after merging vertexes $M_{i+2^{\wedge}\{k-1\}+1,u}$ and $M_{i+2^{\wedge}\{k-1\},d}$. Note that the simplified module graph of markers is similar to the FIG. 6 module graph of linkers.

FIG. 16 shows PCR typing of the recombination product of FIG. 15. Fluorescent marker screening was used to confirm that the strains were recombined correctly, and the strains were further verified in each step by PCR. The purpose of this recombination is to duplicate the copy number of a Janelia LexA transgene (R82C10-LexA). The arrows in the left panel indicate the directions and binding sites of primers. For example, the design shown includes HS1f on AD1 and JT1r on transgene R82C10-LexA. The transgene with AD1 insertion shows a PCR band in the right panel. The transgene with AD2 and the duplicated transgene were similarly confirmed to be correct.

FIG. 17 (SEQ ID NOs: 3-6) shows the sequence of mutations on gRNA cutting sites in {AD1*} and {AD2*}. The bolded letters are the gRNA cutting sites in {AD1} and {AD2}. The underlined letters are the protospacer adjacent motif (PAM) of the gRNA cutting sites. In the corresponding sequences of {AD1*} and {AD2*}, the lower-case letters represent that the bases were mutated, and the dashes represent that the bases were deleted.

FIG. 18 illustrates an experimental design used to test whether the linker and residual linker are orthogonal. {AD1*} and {AD2*} are adaptors 1 and 2 with a mutation on the gRNA cutting sites. With these mutations, the two adaptor mutants cannot be cut by the corresponding Cas9/gRNA. These two mutations mimic residual linkers which have the same homologous sequence as linkers but do not contain the gRNA cutting sites.

FIG. 28 is an illustration of vector-specific adaptor insertion. The vector-specific design allows the provided system to insert the adaptor into all the transgenes with the same vector backbone. In some embodiments, the vector-specific design can be selected to reduce the residual sequence.

FIG. 29 is an illustration of locus-specific adaptor insertion. The locus-specific design allows the provided system to insert the adaptor into all the transgenes at the same genomic locus.

FIG. 32 shows the orthogonality of the marker in the recombinator of FIG. 31. The phenotype of the transgene with an adaptor is generally distinguishable from the phenotypes of undesired genotypes, but it is not necessary to distinguish undesired genotypes from each other by their phenotype.

FIG. 33 shows the simplified orthogonality of the markers in the adaptors and recombinators of FIGS. 31 and 32.

FIG. 34 presents a diagram of the marker genotype in one step of recombination, showing the orthogonality of markers in the adaptors and recombinators used in the coordination recombination strategy. The transgene is first crossed with upstream and downstream recombinator (($M_{i,u}$,$M_{i,Ru}$) and ($M_{i,Rd}$,$M_{i,d}$)); and then, the transheterozygote was crossed with a wild-type strain (or a balancer strain). In the last generation, the transgene with both upstream and downstream adaptors is selected. Undesired genotypes are in gray FIG. 35 shows the orthogonality of the marker in the recombinator of FIG. 34. The phenotype of the transgene with an adaptor is generally distinguishable from the phenotypes of undesired genotypes, but it is not necessary to distinguish undesired genotypes from each other by their phenotype.

FIG. 36 presents inequalities showing the simplified orthogonality of the markers in the adaptors and recombinators of FIGS. 34 and 35 if the marker in the transgene is used for distinguishing.

FIG. 37 presents a graph showing the simplified orthogonality of the markers in the adaptors and recombinators of FIGS. 34 and 35 if the marker in the transgene is used for distinguishing.

FIG. 38 presents inequalities showing the simplified orthogonality of the marker in the adaptors and recombinators of the FIGS. 34 and 35 if the marker in the transgene is not used for distinguishing.

FIG. 39 presents a graph showing the simplified orthogonality of the marker in the adaptors and recombinators of the FIGS. 34 and 35 if the marker in the transgene is not used for distinguishing.

FIG. 53 is a cross diagram of the recombination of FIG. 52, showing how the desired progeny from each cross is selected by screening for corresponding transgenic markers. The existence (+) or absence (−) of an RFP or GFP marker is designated as R+/− or G+/−.

FIG. 54 is an illustration of the application of the provided methods to make a tandem version of the fluorescent voltage indicator {Ace2N}×2. PCR confirms the successful generation of {Ace2N}×2.

FIG. 55 presents example images showing the expression of the fluorescent indicator from FIG. 54 using Ace2N or {Ace2N}×2 driven by the dopamine neuron (DAN) driver R82C10.

FIG. 56 presents plotted comparisons of average intensity and signal-to-noise ratio of the FIGS. 54 and 55 recombinations, showing Ace2N and {Ace2N}×2 in DAN-α'2α2 and DAN-γ2α'1, using a Kruskal-Wallis one-way ANOVA (*: P<0.05, ***: P<0.001).

FIG. 62 shows the fluorescent pattern of the strains used to test the efficiency of recombining 4 transgenes. The 4 transgenes A, B, C, and D are the pan-neuronal genetic drivers and fluorescent genetic markers (A: 10×UAS-IVS-myr::tdTomato; B: R57C10-GAL4; C: 13×LexAop2-mCD8::GFP; D: R57C10-LexA). The pan-neuronal genetic drivers R57C10-GAL4 and R57C10-LexA express the fluorescence in the flies' antenna, maxillary palps, proboscis, and brains. The markers in the adaptors are driven by the 3×P3 promoter and expressed in flies' eyes. The distinct expression patterns allow the genotypes of the flies to be inferred from the phenotypes.

FIG. 63 shows the expression of the strain {A,B,C,D} in the brain and ventral nerve cord (VNC), where A is 10×UAS-IVS-myr::tdTomato; B is R57C10-GAL4; C is 13×LexAop2-mCD8::GFP; D is R57C10-LexA.

DETAILED DESCRIPTION

Incorporation of genetic elements from foreign species to generate transgenic organisms in bacteria, fungi, plants, and animals for a variety of applications ranging from food crops, industrial enzymes, basic research, etc., has transformed our life. To achieve complex functions for academic research, agricultural production, or industrial production, it is desirable to create transgenic organisms with multiple transgenic elements. Because of the underlying constraints imposed by genetic linkage and crossing-over, the incorporation of multiple transgenes can be difficult, time-consuming, and largely limited to one transgene. Harnessing the recent advancement in CRISPR/Cas9 technology, the inventors have developed the provided systems and methods that enable a significant reduction in turnover time for introducing N transgenes in the same locus from $N-1$ to $\log_2 N$ steps. Moreover, this provided strategy surprisingly and advantageously requires the selection of much fewer possible genotypes per step and does not involve embryo injection, thus further reducing labor, cost, and time. The success of the provided systems and methods has been demonstrated as described in the examples herein.

Figure 1:
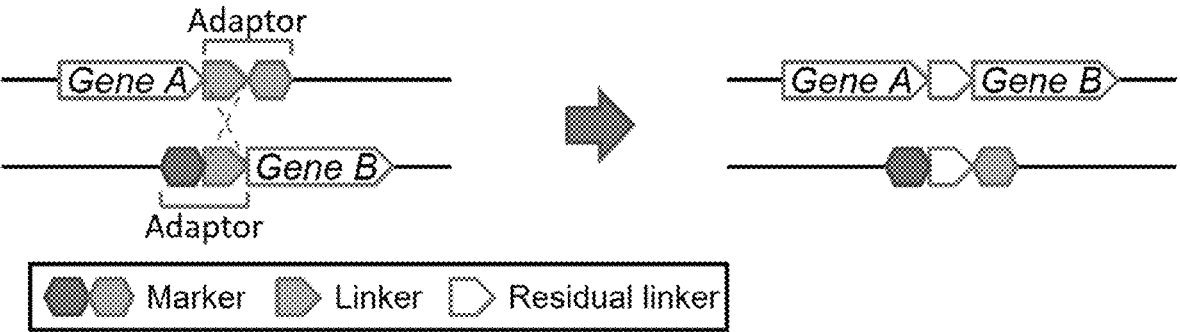
FIG. 1 is an illustration of the composition of adaptors. Each adaptor contains a linker and a marker. The linker is located between the gene to be recombined and the marker. The linker pair facilitates the recombination. After the recombination, the markers are removed from the transgene. This configuration helps distinguish the recombination products from the original transgenes with adaptors.

In certain aspects, using the provided materials and methods, for a given pair of transgenic elements (on the same locus or different loci very close by) to be recombined, adaptor sequences are first added upstream or downstream of each element as shown in FIG. 1. The pair of adaptors then facilitates the integration of the two transgenes into a single, large transgene at one locus. The efficiency of this recombination system is dramatically higher than that of natural recombination. Each adaptor contains two components: a linker and a marker, which are designed using the following principles.

The linkers of the provided adaptors facilitate the recombination of the transgenic elements at the targeted genomic locus and prevent undesired recombination. There can be a residual sequence left after this recombination. Thus, the linkers can be designed to minimize the influence of the residue sequence on the subsequent recombination steps. The orthogonality of a linker is defined by the ability of the linker to only recombine with its paired counterpart but not with a linker from other linker pairs. The number of orthogonal linker pairs in the provided designs depends on the type of recombination strategy to be used. In an activation recombination strategy, only one pair of linkers is used. In a coordination recombination strategy, three or more orthogonal linker pairs are used.

The markers of the provided adaptors are configured to enable straightforward screening for the recombination products, easily distinguishing them from unassembled or misassembled transgenic fragments. The maker can be, for example, a fluorescent protein, an antibiotic-resistant gene, or an amino acid metabolic gene. Within each of the provided adaptors, the linker is located between the maker and the gene to be recombined. After the recombination, the markers are removed to prevent them from influencing subsequent recombination steps. Marker orthogonality is desired for distinguishing transgenesis phenotypes. The number of orthogonal makers required for each provided design also depends on the recombination strategy to be used. In the activation recombination strategy, two orthogonal markers are preferably used to distinguish the two adaptors. In the coordination recombination strategy, three or more orthogonal markers are used.

In some embodiments, the markers are fluorescent markers. Fluorescent proteins suitable for use as the fluorescent markers include, for example, RFP, GFP, and CFP. Fluorescent proteins can be selected for the ease with which their emission light can be distinguished.

In some embodiments, different promoters and enhancers drive cell-specific expressions in multicellular organisms. These promoters can be used to, for example, express fluorescent proteins in different parts of the body. For example, the 3×P3 promoter drives expression in insect eyes (G. Sheng et al., 11 Genes Dev. 1122 (1997); A. J. Berghammer, M. Klingler & E. A. Wimmer, 402 Nature 370 (1999); the 10×STAT92E promoter drives expression in insect eyes (not as strong as 3×P3) and abdomen (E. A. Bach et al., 7 Gene Expr. Patterns 323 (2007)); the 4×Or71a promoter drives expression in insect maxillary palp (A. Ray, W. van der Goes van Naters & J. R. Carlson, 6 PLoS Biol. e125 (2008)); the TpnC41C promoter drives expression in the insect tubular muscles in the thorax (M. B. Chechenova, S. Maes, & R. M. Cripps, 10 PLoS One e0144615 (2015)); and the r4 promoter drives expression in the insect adipose tissue (W. An & P. C. Wensink, 9 Genes & Development 256 (1995)). Thus, by combining $N_c$ different cell-specific promoters and $N_f$ different fluorescent proteins, $N_c N_f$ orthogonal markers can be generated.

In some embodiments, different subcellular localization signals are used as orthogonal markers in unicellular organisms or cell lines. For example, nuclear localization signal (NLS), nuclear export signal (NES), and plasma membrane localization signal can be used to guide a fluorescent protein for localization to different parts of a cell. These distinct fluorescent patterns are easy to identify under the microscope. Thus, by combining $N_s$ different subcellular localization signals and $N_f$ different fluorescent proteins, $N_s N_f$ orthogonal markers can be generated.

In some embodiments, different antibiotic-resistant genes and amino acid metabolic genes are used as orthogonal markers for artificial selection. For example, URA3, LEU2, and HIS3 can be used as selectable markers in yeast. Auxotrophic strains of yeast are not able to synthesize a particular organic compound required for its growth. For example, URA3$^{-/-}$, LEU2$^{-/-}$, and HIS3$^{-/-}$ strain can be easily maintained when grown on media containing the missing nutrients (pyrimidine, L-leucine, and L-histidine). When grown on media not containing the nutrient, however, the host cells will die unless they have incorporated the plasmid carrying the required gene. These markers are orthogonal.

EXAMPLES

The present disclosure will be better understood in view of the following non-limiting examples. The following examples are intended for illustrative purposes only and do not limit in any way the scope of the present invention.

Figure 2:
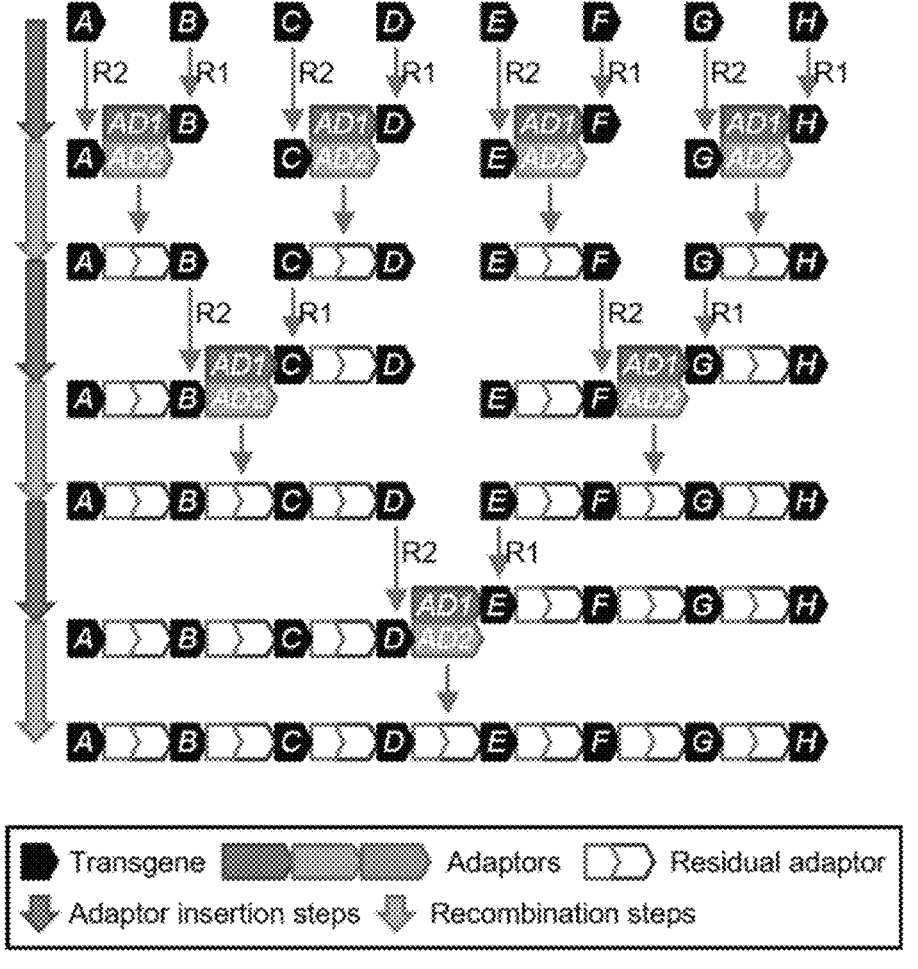
FIG. 2 is an illustration of the activation recombination strategy. In each activation-recombination cycle, a pair of transgenic tandems to be recombined is first activated by adding a pair of adaptors to their terminals. The adaptor pair then leads the two transgenic tandems to be recombined into a larger transgenic tandem.

Example 1. Transgene Recombination Using the Activation Recombination Strategy The provided activation recombination strategy can be used for recombining transgenes from a transgenic library with standard upstream and downstream sequences. An illustration of an exemplary embodiment of this method is shown in FIG. 2. In the first step of this approach, the downstream terminal of one transgene is "activated" by adding an adaptor, and another transgene's terminal is "activated" by adding another adaptor. In the second step, the adaptor pair is used to facilitate the combination of these two transgenes into a large transgene in tandem. The resulting tandem transgene product has its upstream and downstream identical to the original individual transgenes. Thus, the adaptor can be added to the large transgenic tandem to recombine more transgenic elements. To recombine N transgenes, the activation recombination strategy thus uses alternate $\log_2$ N adaptor insertion steps and $\log_2$ N recombination steps, giving 2 $\log_2$ N steps in total.

The activation recombination strategy requires only one pair of adaptors. In each round of the recombination, only one terminal of each transgene is activated by an adaptor. The matching linkers from the adaptor pair then facilitate the recombination at this terminal. Therefore, it is not necessary to design additional orthogonal linkers to prevent the two transgenes from being recombined in an incorrect order. After the recombination, the two transgenes form a large transgenic tandem and drop off the markers in the adaptors. Thus, the markers from the adaptors do not influence the next round of recombination. Optionally, only one type of marker is required for screening, although in some cases, two orthogonal markers are used to distinguish the upstream and downstream adaptors.

Example 2. Transgene Recombination Using the Coordination Recombination Strategy An illustration of an exemplary embodiment of the provided coordination recombination strategy is shown in FIG. 3. In the first step of this approach, all of the upstream and downstream adaptors are added to all the transgenes in a library. Alternatively, a transgenic library is directly created with adaptors on both ends of the transgenes. To recombine N transgenes, the coordination recombination strategy contains two adaptor insertion steps and $\log_2$ N recombination steps, giving 2+$\log_2$ N steps in total. Therefore, when N>4, the coordination recombination strategy requires fewer steps for adding adaptors than the activation recombination strategy of Example 1.

The coordination recombination strategy, however, needs more than one orthogonal adaptor pair and requires its adaptor to be well "coordinated" to ensure correct recombination and screening in every step. Despite this coordination initially appearing to be complicated and to need more orthogonal adaptor pairs as the number of transgenes increases, it was found that only three orthogonal adaptor pairs are required to coordinate the recombination of any number of transgenes. As shown in FIG. 3, the upstream adaptor in adaptor pair j−1 ($AD_{j-1,u}$) and the downstream adaptor in adaptor pair j ($AD_{j,d}$) are added to the transgene i, where i−j is divisible by 3. That is: $AD_{3,u}$ and $AD_{1,d}$ are added to transgene 1, 4, 7, 10, . . . ; $AD_{1,u}$ and $AD_{2,d}$ are added to transgene 2, 5, 8, 11, . . . ; and $AD_{2,u}$ and $AD_{3,d}$ are added to transgene 3, 6, 9, 12, . . . . The approach for coordinating the orthogonal adaptors contains 4 steps: 1) drawing the diagram of genetic crosses; 2) deriving the orthogonality among linkers or markers from the diagram of genetic crosses; 3) converting the orthogonality among linkers or markers into a graph labeling problem; and 4) solving the graph labeling problem to find minimum linker or marker number and labeling pattern. Further details of the approach to deriving the adaptor pattern are provided in Example 3 and Example 4.

The adaptors upstream of the first transgene and downstream of the last transgene are optional. In some embodiments where the final recombination products are intended to be used for further recombination, it can be advantageous to add these adaptors. In other embodiments, it can be preferable not to add these adaptors, thereby avoiding the presence of markers in the final recombination product. When $\log_2$ N is not an integer, designing the recombination processes may be complicated, and a package of computer programs can be used to optimize the recombination processes.

Example 3. Derivation of the Minimum Number of Linkers Required for the Coordination Recombination Strategy To assemble $N_{transgene}$ transgenes, $\log_2 N_{transgene}$ steps of recombination are required. In step k, transgene tandems {transgene i+1, transgene i+2, . . . transgene i+2$^{k-1}$} are recombined with {transgene i+2$^{k-1}$+1, transgene i+2$^{k-1}$+2, . . . transgene i+2$^k$} to form a larger transgene tandem {transgene i+1, transgene i+2, . . . transgene i+2$^k$} (k=1, 2, 3, . . . , $\log_2 N_{transgene}$; i=0, 2$^k$, 2×2$^k$, . . . , $N_{transgene}$−2$^k$). Assuming the recombinating $N_{transgene}$ transgenes need $N_{linker}$ linkers, an ordered integer pair ($L_{i,u}$, $L_{i,d}$) is used to represent the linkers of transgene i (i=1, 2, 3, . . . , $N_{transgene}$; $L_{i,u}$, $L_{i,d}$∈{1, 2, 3, . . . , $N_{linker}$}), where $L_{i,u}$ and $L_{i,d}$ are the index of the upstream and downstream linker of transgene I, respectively. Because the downstream linker of transgene i should match the upstream linker of transgene i+1, $L_{i,d}$= $L_{i+1,u}$. Using the equation $L_{i,d}$=$L_{i+1,u}$=$l_i$ allows the ($L_{i,u}$, $L_{i,d}$) to be simplified to:

$$(l_{i-1}, l_i)$$

$$(i=1,2,3, . . . , N_{transgene}; l_i \in \{1,2,3, . . . , N_{linker}\}).$$

As shown in FIG. 4, in recombination step k, the transgene tandems with linkers ($l_i$, $l_{i+2^{\{k-1\}}}$) and ($l_{i+2^{\{k-1\}}}$, $l_{i+2^k}$) are recombined to form a larger transgene with linker:

$$(l_i, l_{i+2^k})$$

$$(k=1,2,3, . . . , \log_2 N_{transgene}; i=0,2^k, 2×2^k, . . . , N_{transgene}−2^k).$$

The necessary and sufficient condition of correct recombination in step k is that the transgene tandem's upstream linker should not react with the downstream linker of itself, and the downstream linker of ($l_{i+2^{\{k-1\}}}$, $l_{i+2^k}$) should not react with the upstream linker of ($l_i$, $l_{i+2^{\{k-1\}}}$). As shown in FIG. 5, this property can be expressed as:

$$l_i \neq l_{i+2^{\{k-1\}}}$$

$$l_{i+2^{\{k-1\}}} \neq l_{i+2^k},$$

$$l_i \neq l_{i+2^k}$$

$$(k=1,2,3, . . . , \log_2 N_{transgene}; i=0,2^k, 2×2^k, . . . , N_{transgene}−2^k).$$

It is immediately apparent that at least three orthogonal linker pairs are required for recombination. As shown in FIG. 6, a graph can be used to indicate the three inequalities that must be satisfied. In this graph, each vertex represents a linker, and each edge indicates the two adjacent vertices should be orthogonal. The linker design is thus transformed into a graph labeling problem. The graph in FIG. 6 is the basic module representing the recombination of a pair of transgenes. As shown in FIG. 7, all the modules are then combined to form a complete graph containing all the orthogonality requirements for recombining the $N_{transgene}$ transgenes. This graph clearly indicates that the orthogonality requirements can be simplified into $$l_i \neq l_{i+2^k}$$

$$(k=0,1,2,\ldots,\log_2 N_{transgene}; i=0,2^k,$$
$$2\times 2^k,\ldots,N_{transgene}-2^k).$$

Here, $l_i=i \pmod 3$ ($l_i \in \{1, 2, 3\}$). In this case, because $i \neq i+2^k \pmod 3$, $l_i \neq l_{i+2^k} \pmod 3$. Thus, $l_i \neq l_{i+2^k}$. This demonstrates that three orthogonal linker pairs are sufficient to mediate the recombination of the transgenes in all the steps.

Example 4. Derivation of the Minimum Number of Markers Required for the Coordination Recombination Strategy In an analysis analogous to that of Example 3, an ordered integer pair ($M_{i,u}$, $M_{i,d}$) can be used to represent the upstream and downstream markers of transgene i (i=1, 2, 3, . . . , $N_{transgene}$; $M_{i,u}$, $M_{i,d} \in \{1, 2, 3, \ldots, N_{marker}\}$). Typically, when examining the phenotype of an organism, one cannot distinguish whether a marker is on the upstream or the downstream of a transgene tandem. Accordingly, the phenotype of a transgene tandem with markers ($M_{i,u}$, $M_{j,d}$) should be represented by the set $\{M_{i,u}\}\cup\{M_{j,d}\}$ (without assuming $M_{i,u} \neq M_{j,d}$). In recombination step k, two transgene tandems with markers ($M_{i+1,u}$, $M_{i+2^{\{k-1\}},d}$) and ($M_{i+2^{\{k-1\}}+1,u}$, $M_{i+2^k,d}$) are recombined as shown in FIG. 8 to form a larger transgene with markers:

$$(M_{i+1,u}, M_{i+2^k,d})$$

$$(k=1,2,3,\ldots,\log_2 N_{transgene}; i=0,2^k,$$
$$2\times 2^k,\ldots,N_{transgene}-2^k).$$

Therefore, to distinguish the product from the unreacted transgene tandem, we require $$\{M_{i+1,u}\}\cup\{M_{i+2^k,d}\}\neq\{M_{i+1,u}\}\cup\{M_{i+2^{\{k-1\}},d}\}$$

$$\{M_{i+1,u}\}\cup\{M_{i+2^k,d}\}\neq\{M_{i+2^{\{k-1\}},1,u}\}\cup\{M_{i+2^k,d}\}.$$

Through use of the CRISPR/Cas9 genome editing system to induce the recombination, to ensure reliability, the phenotype of the product will be different from the phenotypes associated with deletion or Non-Homologous End Joining (NHEJ) mutations. As a result, and as shown in FIG. 9, the following inequalities will hold:

$$\{M_{i+1,u}\}\cup\{M_{i+2^k,d}\}\neq\{M_{i+1,u}\},$$

$$\{M_{i+1,u}\}\cup\{M_{i+2^k,d}\}\neq\{M_{i+2^{\{k-1\}},d}\},$$

$$\{M_{i+1,u}\}\cup\{M_{i+2^k,d}\}\neq\{M_{i+2^{\{k-1\}}+1,u}\},$$

$$\{M_{i+1,u}\}\cup\{M_{i+2^k,d}\}\neq\{M_{i+2^k,d}\},$$

$$\{M_{i+1,u}\}\cup\{M_{i+2^k,d}\}\neq\{M_{i+2^{\{k-1\}},d}\}\cup\{M_{i+2^{\{k-1\}}+1,u}\}$$

$$(k=1,2,\ldots,\log_2 N_{transgene}; i=0,2_k,2\times 2^k,\ldots,$$
$$N_{transgene}-2^k).$$

These can be simplified as shown in FIG. 10 into:

$$M_{i+2^k,d}\neq M_{i+2^{\{k-1\}},d}$$

$$M_{i+1,u}\neq M_{i+2^{\{k-1\}}+1,u}$$

$$M_{i+1,u}\neq M_{i+2^k,d}$$

$$(M_{i+1,u}\neq M_{i+2^{\{k-1\}},d} \text{ or } M_{i+2^k,d}\neq M_{i+2^{\{k-1\}}+1,u})$$

$$(k=1,2,3,\ldots,\log_2 N_{transgene}; i=0,2^k,$$
$$2\times 2^k,\ldots,N_{transgene}-2^k).$$

The above inequalities can be represented by a graph module as in FIG. 11. The two dashed lines in the graph indicate $M_{i+1,u}\neq M_{i+2^{\{k-1\}},d}$ or $M_{i+2^k,d}\neq M_{i+2^{\{k-1\}}+1,u}$. It is not required that both pairs of markers be orthogonal. Before assembling all the graph modules into a complete graph of marker orthogonality, the graph module can first be simplified. Because there is no edge connecting $M_{i+2^{\{k-1\}},d}$, and $M_{i+2^{\{k-1\}}+1,u}$, these can be allowed to have the same label, merging the two vertices in the FIG. 11 graph module in to form the graph of FIG. 12 (where $M_{i+1,u}=M_{i,d}=m_i$ (i=0, 1, 2, . . . , $N_{transgene}$)). Thus, a graph label pattern satisfying the graph in FIG. 12 will also be sufficient to satisfy the graph in FIG. 11. Note that FIG. 12 is similar to FIG. 6. Thus, the requirement for orthogonality of markers is the same as that for linkers, and coordinating of all markers only requires that $m_i=l_i$. The minimum number of linker pairs required for the coordination recombination strategy is three. Thus, the minimum number of markers required for the coordination recombination strategy is also three.

Example 5. Homologous Linker Pair Design

Figure 13:
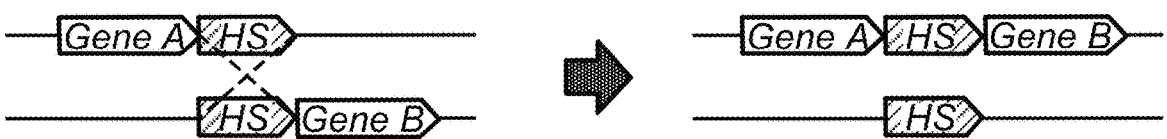
FIG. 13 is an illustration of a homologous linker pair recombined by natural recombination

The simplest adaptor pair design is a pair of homologous sequences, as shown in FIG. 13. Natural homologous recombination can merge two genes with such an adaptor pair. In this design, the homologous sequence will remain after the recombination. The two pairs of adaptors are orthogonal as long as their sequences are significantly different. Thus, different homologous sequences must be used for different adaptors. In some organisms, the recombination rate is high. For example, the average recombination rate of the yeast genome is 340 cM/Mb (R. K. Mortimer, C. R. Contopoulou & J. S. King, 8 Yeast 817 (1992); F. Baudat & A. Nicolas, 94 Proc. Natl. Acad. Sci. USA 5213 (1997)). This means that a 1-kbp homologous sequence will provide a 0.34% recombination rate, which is high enough for screening.

Figure 14:
FIG. 14 is an illustration of a homologous linker pair recombined under nuclease induction.
Figure 15:
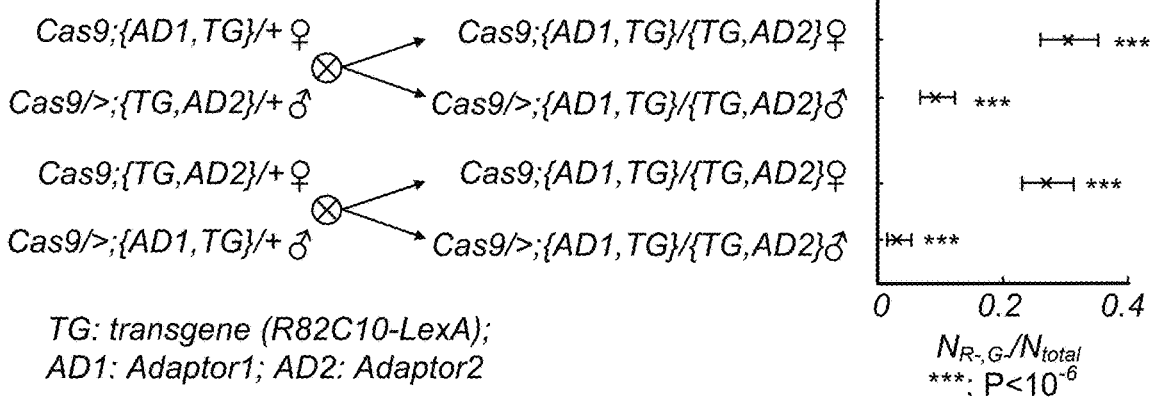
FIG. 15 shows the efficiency of adaptor-mediated recombination, defined as the percentage of the R-, G-animals among all progeny. Accounting for maternal effects, all 4 possible cross designs were tested. The error bars indicate the 95% confidence interval of the efficiency. The insertion efficiency was compared to natural recombination using a binomial test (***: P<10⁻⁶). The efficiency in this step is ~8% for male F3 and ~25% for female F3.

Most multicellular organisms, however, have a much lower recombination rate than fungi. For example, rates of 2 cM/Mb in the fruit fly and 1 cM/Mb in mice have been observed (J. Stapley et al., 372 Philos. Trans. R Soc. Lond. B Biol. Sci. 20160455 (2017)). In this case, the recombination rate must be significantly increased with the use of a nuclease, as shown in FIG. 14. The nuclease cuts the end of the homologous sequence, induces a double-strand break, and triggers DNA repair. One example of a nuclease suitable for use with the methods provided herein is the CRISPR/Cas9 system. For one pair of adaptors, two nucleases with different target sequences are required. To avoid self-cutting, each member of the adaptor pair only contains the nuclease and nuclease target sequence for the nuclease from the other member (FIG. 14). The cutting events only happen when the two adaptors co-exist in the same organism. As shown in FIG. 15, a 1-kb homologous sequence was found to lead to ~17% recombination in the fruit fly, ~10000-fold higher than the natural recombination. The correct recombination of the strains was confirmed by screening for fluorescent markers, and the strains were further verified before and after recombination by PCR (FIG. 16). The arrows in the left panel indicate the directions and binding sites of primers. For example, the design shown includes HS1f on AD1 and JT1r on transgene R82C10-LexA. The transgene with AD1 insertion shows a PCR band in the right panel. The transgene with AD2 and the duplicated transgene were similarly confirmed to be correct.

Figure 52:
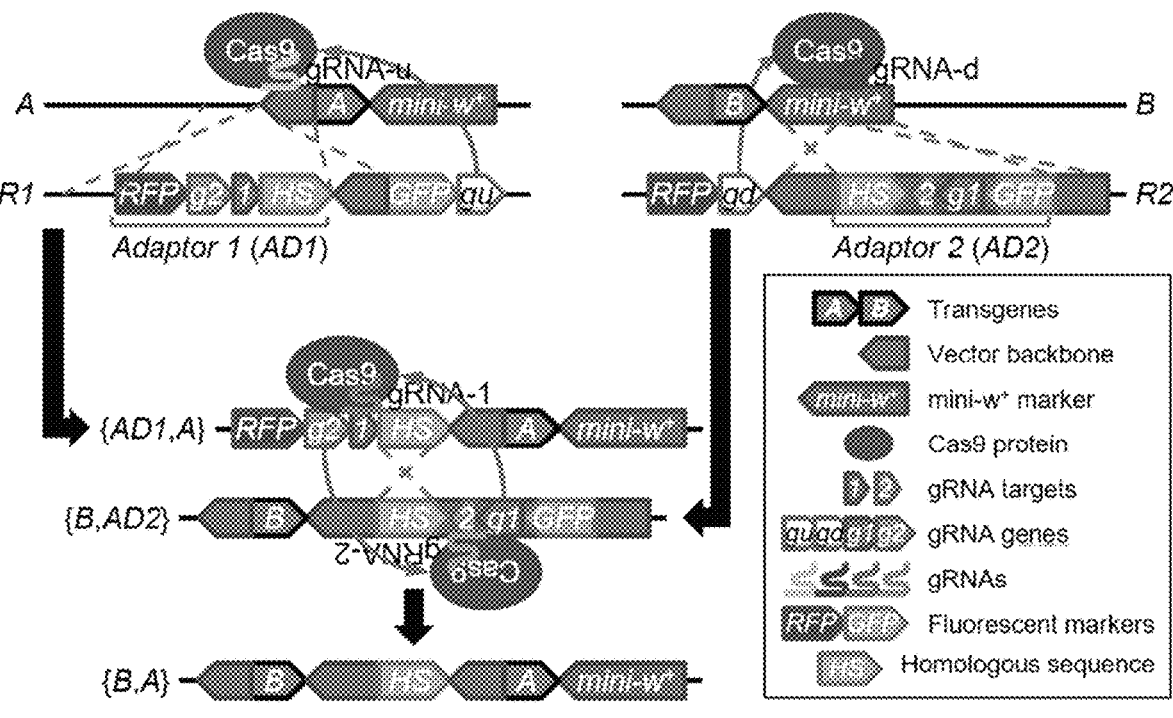
FIG. 52 is an illustration of the use of CRISPR/Cas9 editing with the provided methods to recombine transgenes A and B at the same genomic location in two steps. First, R1 and R2 insert AD1 and AD2 upstream of A and downstream of B, to generate {AD1,A} and {B,AD2}. Second, AD1 and AD2 target each other and mediate the recombination to generate {B,A}.

The insertion of the adaptors with homologous linker pairs, and the inducement of the correct recombination using these adaptors, have been confirmed. FIG. 52 is an illustration of the use of CRISPR/Cas9 editing with the methods provided herein to recombine transgenes A and B at the same genomic location in two steps. In the first step, Recombinator 1 and 2 (R1 and R2) are used to insert AD1 and AD2 upstream of A and downstream of B, generating {AD1,A} and {B,AD2}. In the second step, {AD1,A} is crossed with {B,AD2}. With Cas9 protein, the gRNA-2 encoded in AD1 cut the gRNA-2 target on AD2, and the gRNA-1 encoded in AD2 cut the gRNA-1 target on AD1. The homologous sequences on the adaptor pair then facilitate the integration of the two transgenes into a single, large transgene {B,A} tandem. FIG. 53 is a diagram of the recombination of FIG. 52, showing how the desired progeny from each cross is selected by screening for corresponding transgenic markers. The existence (+) or absence (−) of an RFP or GFP marker is designated as R+/− or G+/−.

A higher level of expression of the voltage indicators usually helps to increase the signal intensity and signal-to-noise ratio. A fluorescent voltage indicator is recombined with itself to double its copy number. FIGS. 30, 54, 55, and 56 show a proof-of-principle experiment for this strategy. The members of the adaptor pair AD1 and AD2 are inserted separately into 13×LexAop-Ace2N::mNeon (Ace2N) and the transgene is duplicated to form a 2× tandem repeat ({Ace2N}×2). Fluorescent marker screening was used to confirm that the strains were recombined correctly, and the strains were further verified in each step by PCR. FIG. 54 shows PCR typing of transgene with adaptor ({AD1, Ace2N} and {Ace2N,AD2}) and the recombination product ({Ace2N}×2). The detailed map of primers for this PCR typing is in FIG. 30. A dopamine neuron (DAN) driver (GMR82C10-LexA) strain was crossed with the one-copy or two-copy Ace2N strain (Ace2N or {Ace2N}×2) to express the Acc2N::mNeon in DAN-α'2α2 and DAN-γ2α'1 (FIG. 55). The voltage-imaging experiments indicated that {Ace2N}×2 significantly improved the fluorescent intensity and signal-to-noise ratio comparing to Ace2N (FIG. 56). This approach can be used on the genetic drivers or other indicators to improve their function.

Figure 19:
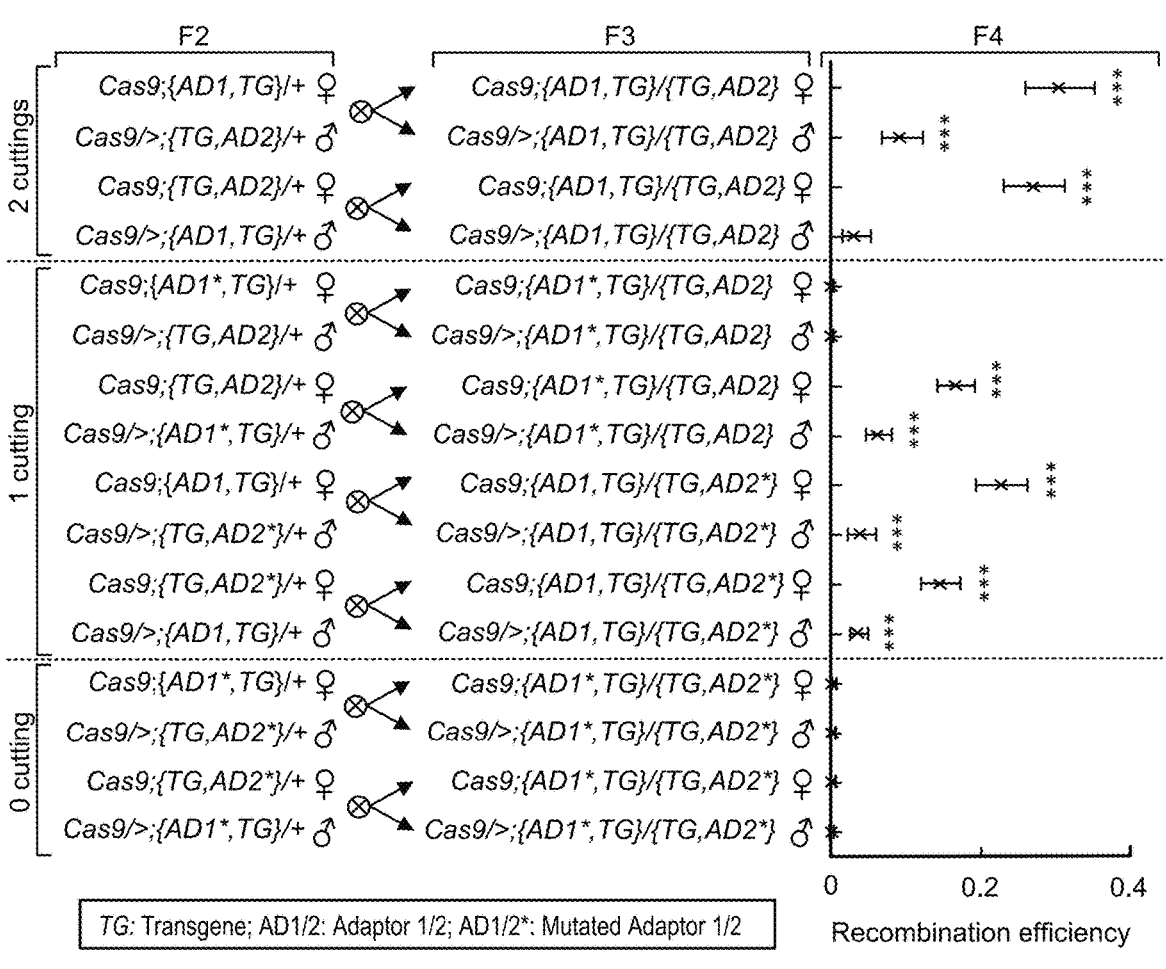
FIG. 19 shows the efficiency of adaptor-mediated recombination, defined as the percentage of the R-, G-animals among all progeny. Accounting for maternal effects, all 4 possible cross designs were tested. The data of the two cutting cases are identical to those of FIG. 15 and are duplicated here for easier comparison with other cases. The error bars indicate the 95% confidence interval of the efficiency. The insertion efficiencies are compared to natural recombination using a binomial test (***: P<10⁻⁶). Recombination between a normal linker and a mutated linker is also observed, but a pair of the mutated linker cannot induce recombination.

In the homologous linker pair design, the nuclease cutting site is located between the homologous sequence and the nuclease coding gene, so that the nuclease genes are removed after the recombination. The cutting site of the Cas9/gRNA nuclease is inside of the nuclease target sequence, so the nuclease target sites are disrupted after the cutting. Only the homologous sequence is left after the recombination (FIG. 14). Further experiments also indicated that the presence of both nuclease cutting events is not necessary for the recombination (FIGS. 17, 18 and 19). One nuclease cutting event can induce the recombination on the homologous sequences (FIGS. 17, 18, and 19). Although lacking the nuclease cutting site, the homologous sequence left after previous recombination steps may recombine with adaptors in the following steps. Therefore, when the transgenic tandems to be recombined contain the same homologous sequence as the adaptors, it is not sufficient to screen for the correct recombination products simply by the markers in the adaptors. Rather, additional PCR steps are required to confirm the correct recombination products. This suggests the benefit of an alternative orthogonal adaptor pair design using different homologous sequences with different nucleases and their cutting sites.

Figure 62:
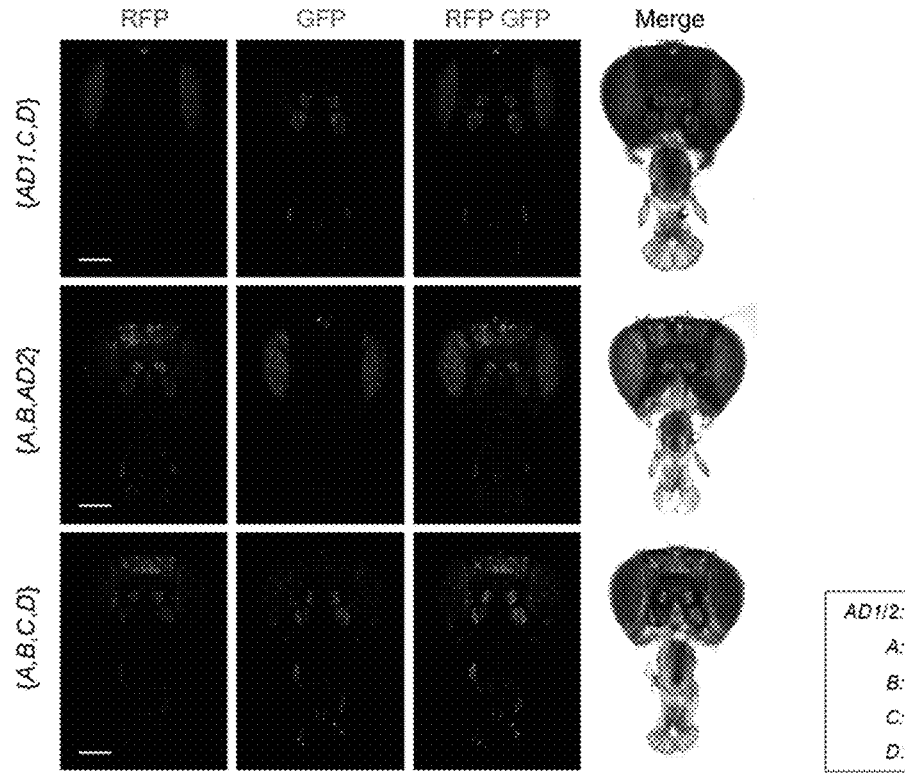
As shown in FIGS. 62 and 63, their expression patterns are different from the fluorescent markers in the adaptors labeled as $R^{AD}$ and $G^{AD}$. Because the homologous linkers in the adaptors are not perfectly orthogonal to the residual homologous sequence left by previous recombinations, the recombination produces four possible products which are not distinguishable merely based on the mini-w⁺ marker and the fluorescent markers in the adaptors $(w^+R^{AD-}G^{AD-})$. Here, $w^+R^{AD-}G^{AD-}$ represents that the flies showed the mini-w⁺ marker but did not show the red or green fluorescent markers in the adaptors
Figure 63:
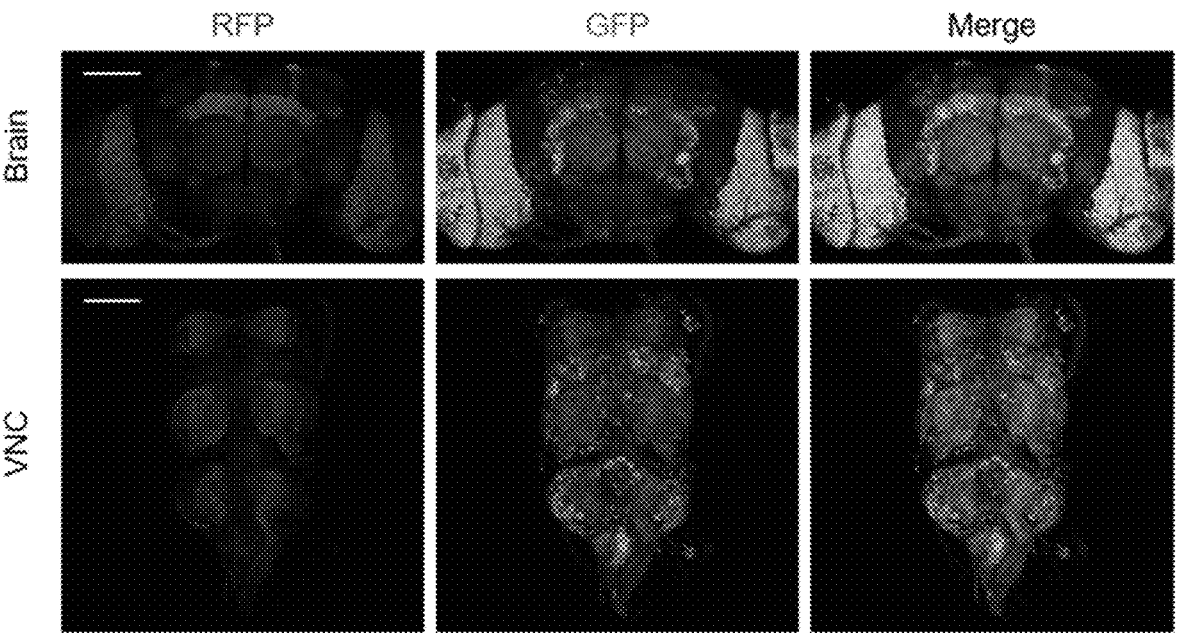

To demonstrate the homologous linker pair can continuously recombine the transgenic tandems, two pan-neuronal genetic drivers R57C10-GAL4 and R57C10-LexA (transgene A and C in FIG. 62) and two genetic fluorescent indicators 10×UAS-IVS-myr::tdTomato and 13×LexAop2-mCD8::GFP (transgene B and D in FIG. 62) were recombined in two rounds of recombination. In the first round of the recombination, the 4 transgenes were recombined into 2-transgenic tandems: {A,B} and {C,D}. In the second round of recombination, the 2-transgenic tandems with adaptors ({A,B,AD2} and {C,D,AD1}) were created and then recombined to form the 4-transgenic tandem {A,B,C,D}. Here, the fluorescent phenotypes enabled convenient detection of the genotypes of the recombination products. As shown in FIG. 62, the fluorescent patterns driven by the pan-neuronal genetic drivers were obviously different from the fluorescent markers in the adaptors. With these markers, it was confirmed that the 4-transgenic tandem was successfully recombined (FIGS. 62 and 63).

Figure 20:
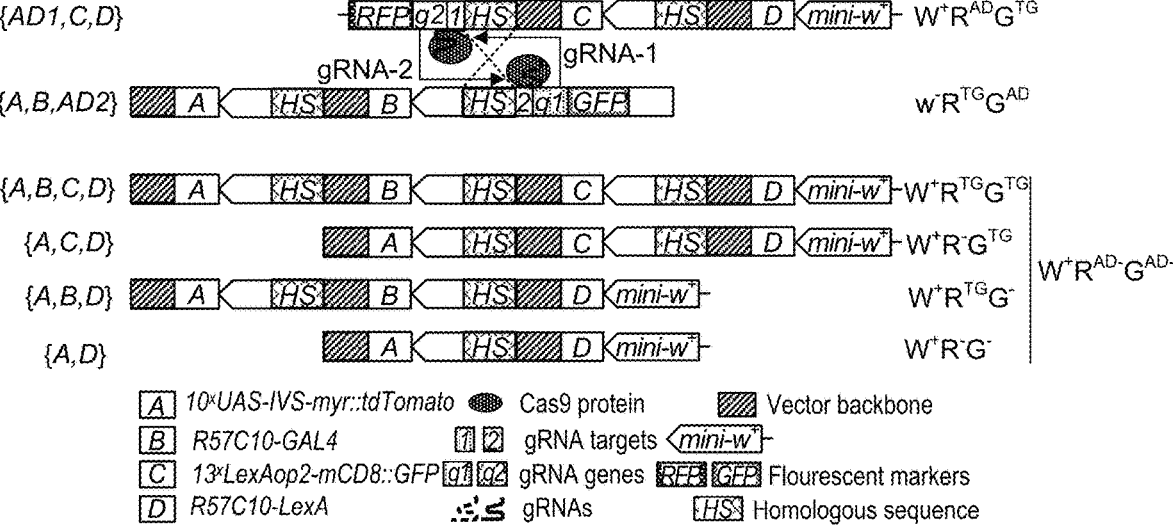
FIG. 20 illustrates the experimental design to detect the correct recombination rate when we recombine 4 transgenes. The transgenes A, B, C, and D are pan-neuron drivers and fluorescent reports. The genotypes and phenotypes of the transgenic tandems are shown on the left and right sides of their maps. Combining transgenes A and B drives red fluorescence in neurons. Combining transgenes C and D drives green fluorescence in neurons. These two phenotypes are labeled as $R^{TG}$ and $G^{TG}$.

To directly measure how much the residual homologous sequence will influence the following recombination, an experiment was designed to measure the efficiency and correct recombination rate in recombining 4 transgenes with homologous linker pair (FIG. 20). These fluorescent phenotypes driven by pan-neuronal drivers are labeled as $R^{TG}$ and $G^{TG}$ to distinguish from the fluorescent phenotypes driven by the markers in the adaptors, which are labeled as $R^{AD}$ and $G^{AD}$. Because the homologous linkers in the adaptors are not perfectly orthogonal to the residual homologous sequence left by previous recombinationsm there were four possible recombination products: {A,B,C,D}, {A,C,D}, {A,B,D}, and {A,D} (FIG. 20). These could not be distinguished merely based on the mini-w$^+$ marker and the fluorescent markers in the adaptors (w$^+$R$^{AD-}$G$^{AD-}$) (FIG. 20), but phenotypes caused by the transgenes can be used to detect proportions of the four possible recombination products.

Figure 21:
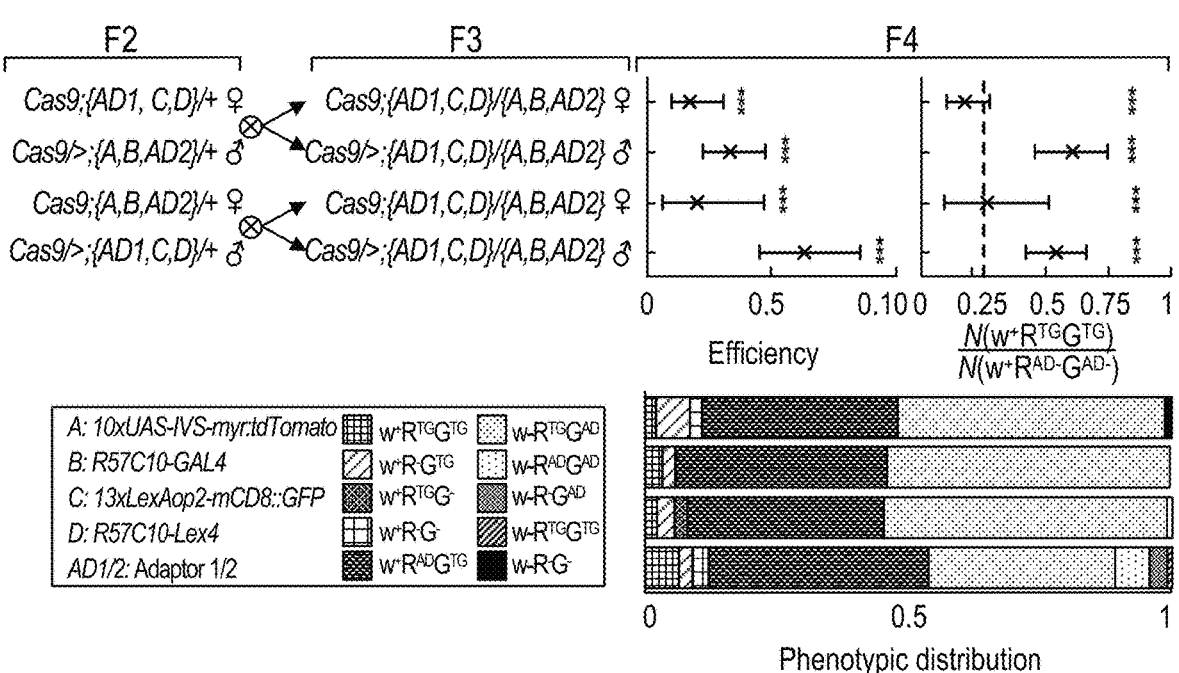
FIG. 21 shows the results of recombining 4 transgenes by the homologous linker pair. The efficiency is defined as the proportion of $w^+R^{TG}G^{TG}$ flies in the total F4 progeny. Accounting for maternal effects, all 4 possible cross designs were tested. The error bars indicate the 95% confidence interval of the efficiency. The recombining efficiency was compared to natural recombination using a binomial test (*: P<10⁻⁶). The correct recombination rate is defined as the number of $w^+R^{TG}G^{TG}$ flies divided by the number of $w^+R^{AD-}G^{AD-}$ flies. If the 4 recombination products with $w^+R^{AD-}G^{AD-}$ phenotype appeared with equal probability, the correct recombination rate should be 25% (dashed line). The correct recombination rates are compared with the baseline (25%) by binomial test (*: $P<10^{-6}$). The correct recombination rates of the progeny of F3 males were significantly higher than 25%. The bar graph indicates the distributions of the F4 progeny's phenotypes. In F4, we observed all 4 recombination products shown in FIG. 20, including $w^+R^-G^-$ flies.

Accounting for maternal effects, all 4 possible cross designs were tested. The recombination efficiencies (the proportion of w$^+$R$^{TG}$G$^{TG}$ flies in the total F4 progeny) of the 4 cross designs were 2-6%, significantly higher than the natural recombination (FIG. 21). The correct recombination rate was also calculated as the number of w$^+$R$^{TG}$G$^{TG}$ flies divided by the number of w$^+$R$^{AD-}$G$^{AD-}$ flies (FIG. 21). If the 4 recombination products with w$^+$R$^{AD-}$G$^{AD-}$ phenotype appear with equal probability, the correct recombination rate will be 25%. The correct recombination rates were compared with the baseline (25%, the dashed line in FIG. 21) by binomial test. The correct recombination rates of the progeny of F3 males were significantly higher than 25% (FIG. 21). This means the F3 males have a higher probability of reproducing the 4-transgenic tandems than other recombination products. The bar graph indicates the distributions of the F4 progeny's phenotypes. All 4 recombination products shown in FIG. 20 were observed in F4, including w$^+$R$^-$G$^-$ flies. Even though generally the 4-transgenic tandem should not be screened for merely based on the markers in the adaptor, the false positive rate of the screening is limited. Only a few more PCR screenings are required to select the correct 4-transgenic tandem flies from the w$^+$R$^{AD-}$G$^{AD-}$ flies, because about 50% of the w$^+$R$^{AD-}$G$^{AD-}$ progeny from F3 males are the desired products.

Example 6. AttP/attB Linker Pair Design

Figure 22:
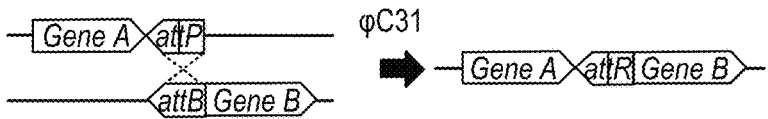
FIG. 22 is an illustration of an attP/attB linker pair recombined by φC31.

The CRISPR/Cas9 system creates DNA double-strand breaks, which may cause complicated on-target mutations, including large deletion and genomic rearrangements (M. Kosicki, K. Tomberg & A. Bradley, 36 Nat. Biotechnol. 765 (2017)). To exclude the unexpected recombinations, special genotyping screening is generally required. Another option is using an adaptor pair based on the attP/attB system catalyzed by unidirectional recombinase (FIG. 22). Because the recombinase stabilizes the intermediate state of recombination and significantly reduces the accessibility of the endogenous DNA repair system to the DNA double strain break, the products of the attP/attB linker can be more controllable. For example, the recombinase φC31 mediates the DNA strand exchange on the attP/attB sequence pair and forms the attL/attR. In this design, only the attL or attR will be left after the recombination (FIG. 22). φC31 does not catalyze any other att pairs other than attP and attB (H. M. Thorpe & M. C. Smith, 95 Proc. Natl. Acad. Sci. USA 5505 (1998); L. C. Thomason, R. Calendar & D. W. Ow, 265 Mol. Genet. Genomics 1031 (2001)). Thus, the recombination on the linker pair is unidirectional, and the residual sequence after recombination does not influence the following recombination steps.

Figure 57:
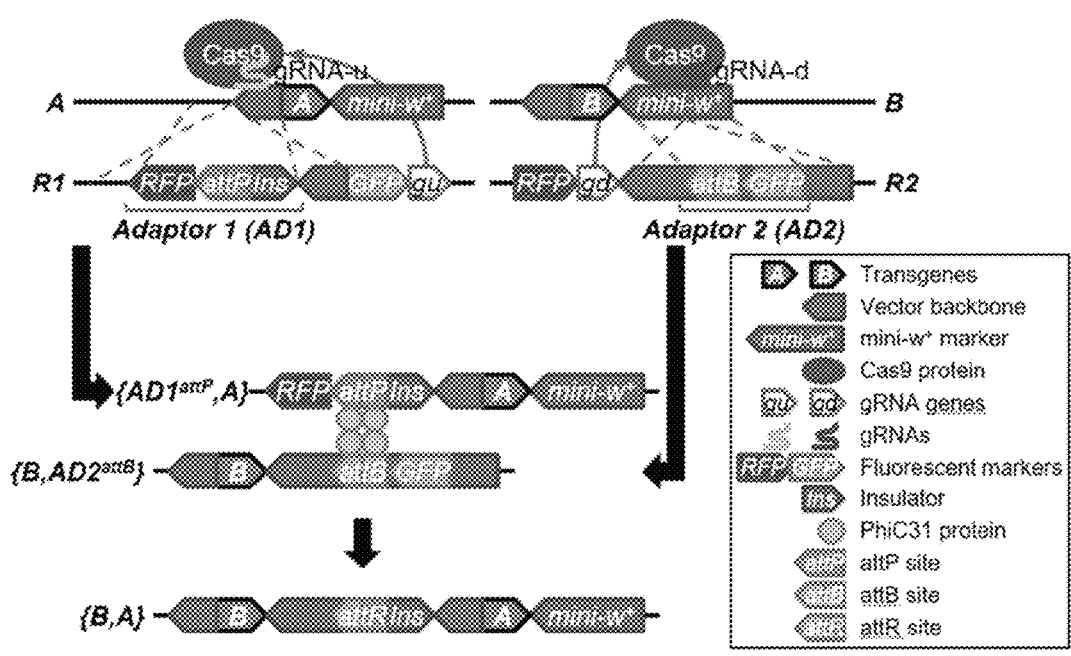
FIG. 57 is an illustration of the use of CRISPR/Cas9 editing and QC31 with the provided methods to recombine transgenes A and B at the same genomic location in two steps.
Figure 58:
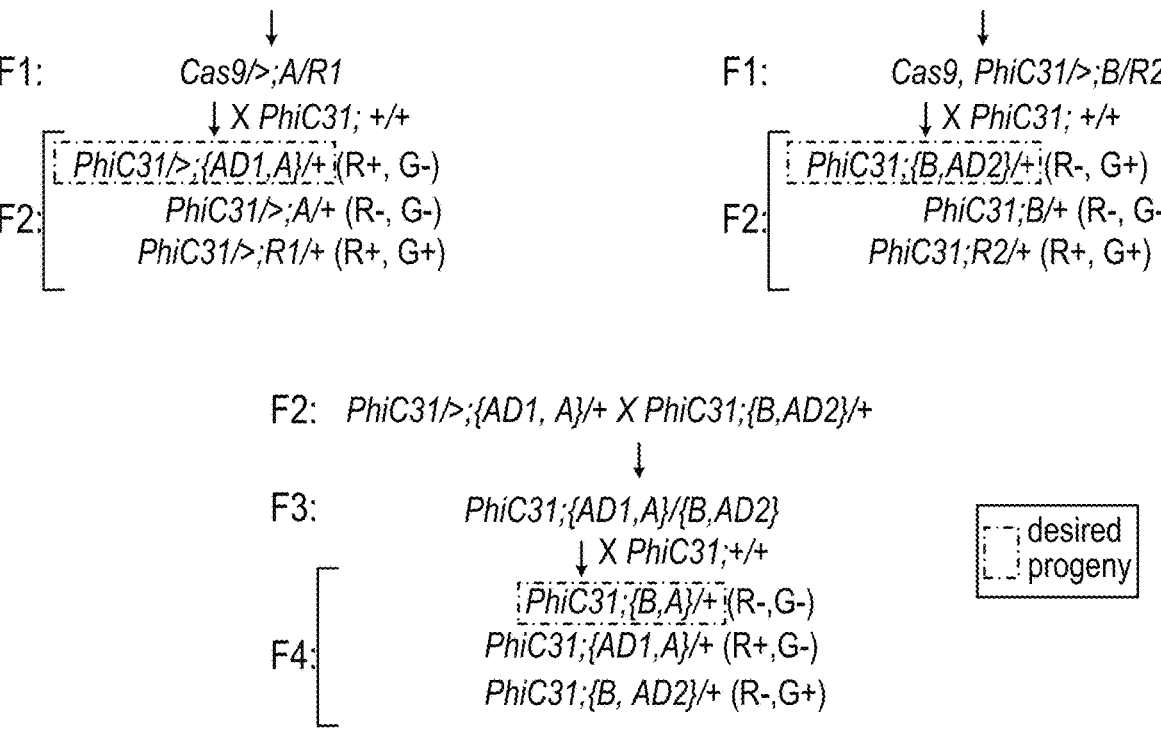
FIG. 58 is a cross diagram of the recombination of FIG. 57, showing how the desired progeny from each cross is selected by screening for corresponding transgenic markers. The existence (+) or absence (−) of an RFP or GFP marker is designated as R+/− or G+/−.

The insertion of the adaptors with attP/attB linker pairs, and the inducement of the correct recombination using these adaptors, have been confirmed. FIG. 57 is an illustration of the use of CRISPR/Cas9 editing and QC31 with the methods provided herein to recombine transgenes A and B at the same genomic location in two steps. In the first step, R1 and R2 are used to insert AD1$^{attP}$ and AD2$^{attB}$ upstream of A and downstream of B, generating {AD1$^{attP}$,A} and {B,AD2$^{attB}$}. In the second step, φC31 targets AD1$^{attP}$ and AD2$^{attB}$ and mediates the recombination to generate {B, A}. FIG. 58 is a diagram of the recombination of FIG. 57, showing how the desired progeny from each cross is selected by screening for corresponding transgenic markers. The existence (+) or absence (−) of an RFP or GFP marker is designated as R+/− or G+/−.

Figure 59:
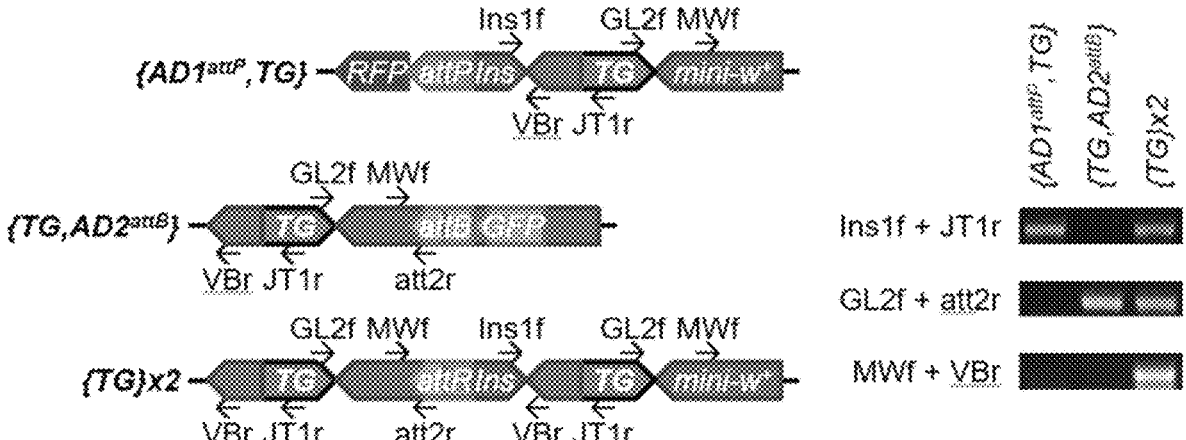
FIG. 59 is an illustration showing PCR typing of the recombination of the attP/attB linker pair of FIGS. 23 and 24.

FIG. 59 shows PCR typing of the recombination product of the attP/attB linker pair. Fluorescent marker screening was used to confirm that the strains were recombined correctly, and the strains were further verified in each step by PCR. This recombination aims to duplicate the copy number of a Janelia LexA transgene (R82C10-LexA). The arrows in the left panel indicate the directions and binding sites of primers. For example, the design shown includes Ins1f on AD1$^{attP}$ and JT1r on R82C10-LexA. The transgene with AD1$^{attP}$ insertion shows a PCR band in the right panel. The transgene with AD2$^{attB}$ and the duplicated transgene were similarly confirmed to be correct.

Figure 23:
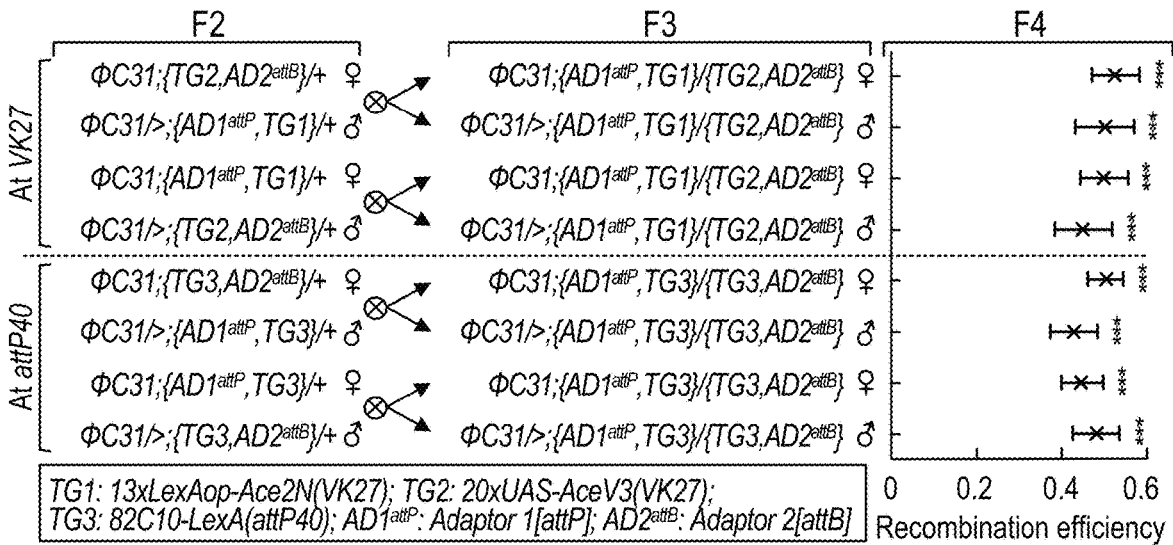
FIG. 23 is a plot showing the recombination efficiency of the attP/attB linker pair of FIG. 22 at different genomic loci (VK27 and attP40). The error bars indicate the 95% confidence interval of the efficiency. The recombining efficiencies are compared to natural recombination using a binomial test (***: $P<10^{-6}$). The average recombination efficiency is ~48%, close to the theoretical limit (50%).

To test the efficiency of the recombination induced by the attP/attB linker pair, the transgenes with AD1$^{attP}$ or AD2$^{attB}$ were created at different genomic loci. These transgenic lines were then crossed and recombined by φC31 (FIG. 23). The efficiency of the recombination in FIG. 23 is defined as the frequency of the progeny without fluorescent markers. FIG. 23 demonstrated that the recombination efficiency of the attP/attB linker pair is significantly higher than natural recombination among various genomic loci. In fact, the average efficiency is ~48% (FIG. 23), which is close to the theoretical limit (50%).

Figure 24:
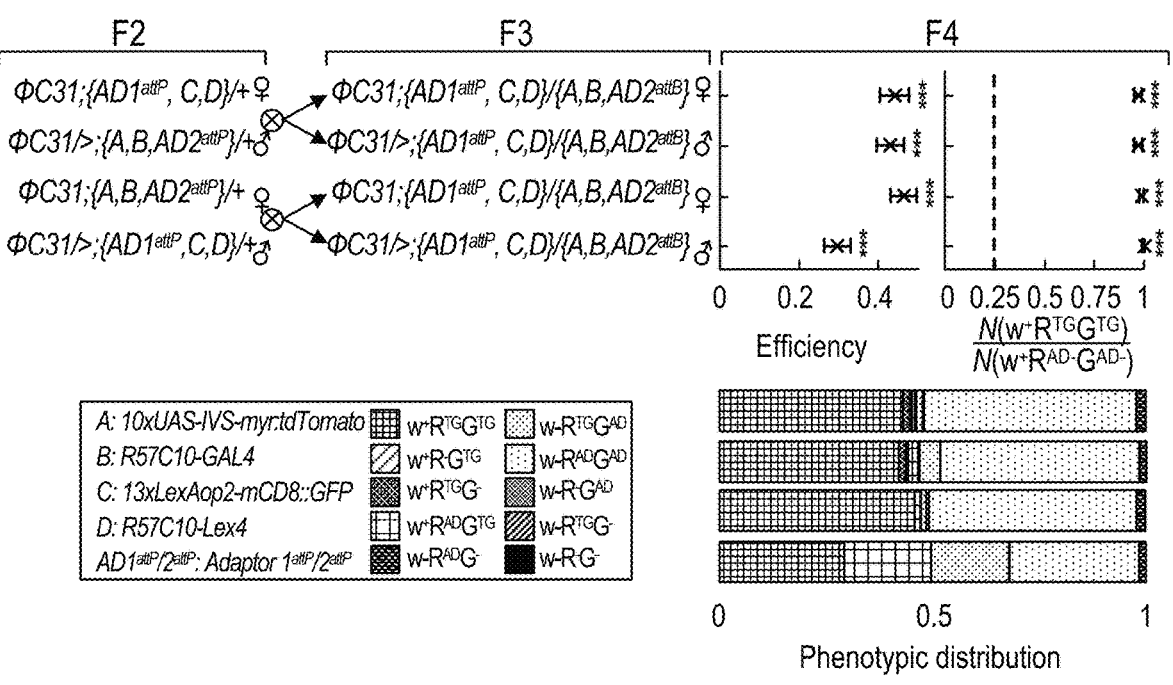
FIG. 24 shows the results of recombining 4 transgenes by the attP/attB linker pair. The efficiency is defined as the proportion of $w^+R^{TG}G^{TG}$ flies in the total F4 progeny. Accounting for maternal effects, all 4 possible cross designs were tested. The error bars indicate the 95% confidence interval of the efficiency. The recombining efficiencies are compared to natural recombination using a binomial test (*: $P<10^{-6}$). The correct recombination rate is defined as the number of $w^+R^{TG}G^{TG}$ flies divided by the number of $w^+R^{AD-}G^{AD-}$ flies. If the 4 recombination products with $w^+R^{AD-}G^{AD-}$ phenotype appear with equal probability, the correct recombination rate should be 25% (dashed line). The correct recombination rates are compared with the baseline (25%) by binomial test (*: $P<10^{-6}$). The correct recombination rates of all 4 cross designs are close to 100%, significantly higher than 25%. The bar graph indicates the distributions of the F4 progeny's phenotypes. In F4, only 3 out of the 4 possible recombination products are observed. No $w^+R^-G^-$ flies are found in F4. The attP/attB linker pair has much higher efficiency and controllability than the homologous linker pair.

The efficiency of recombining 4 transgenes by the attP/attB linker pair (FIG. 24) was also tested. The approach was similar to that used to test the homologous linker pair (FIG. 20). The transgenes to be recombined were also pan-neuronal genetic drivers and fluorescent markers. Accounting for maternal effects, all 4 possible cross designs were tested. The recombination efficiencies (the proportion of w$^+$R$^{TG}$G$^{TG}$ flies in the total F4 progeny) of the 4 cross designs were significantly higher than the natural recombination (FIG. 24). In three of the cross designs, the efficiency of recombining 4 transgenes was not significantly lower than the efficiency of recombining 2 transgenes (FIG. 24). The correct recombination rates of the 4 cross designs were close to 100%, significantly higher than the baseline 25% (FIG. 24). In the F4 progeny, only three of the 4 possible recombination products were observed. The phenotype w$^+$R$^+$G$^−$ did not exist in F4. This indicates that the recombination induced by the attP/attB linker is much more efficient and controllable than the recombination induced by the homologous linker.

Figure 60:
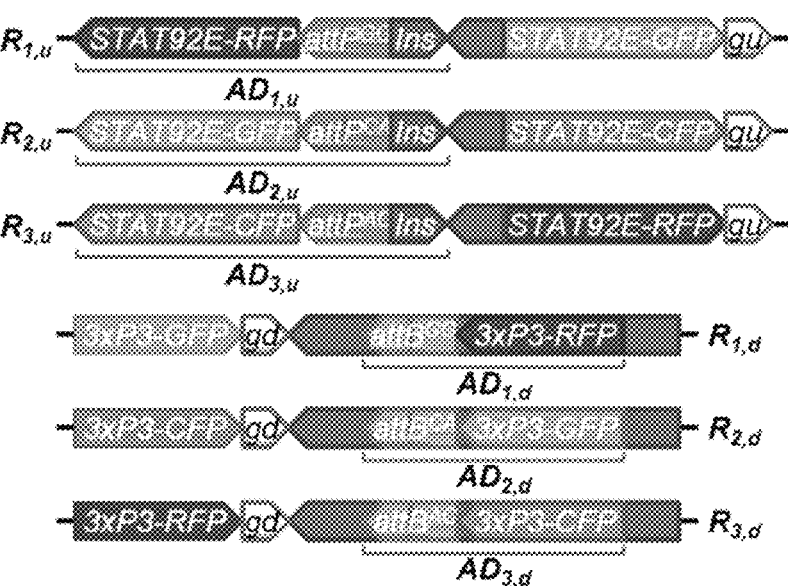
FIG. 60 is an example illustration of maps of recombinators following the designs in FIG. 46. This example uses three orthogonal linker pairs attp$^{GG}$/attB$^{GG}$, attP$^{AC}$/attB$^{AC}$, and attP$^{CA}$/attB$^{CA}$.

As discussed in Example 2, the coordination recombination strategy needs three orthogonal linkers. A set of orthogonal attP/attB pairs can be produced by engineering the core sequence. Wild-type attP and attB have a core "TT" sequence where the recombination occurs. By mutating this core sequence into "GG", an attP$^{GG}$/attB$^{GG}$ pair orthogonal to wild-type attP/attB is generated (B. Blanco-Redondo & T. Langenhan 8 G3 (Bethesda) 3109 (2018); S. D. Colloms, 42 Nucleic Acids Res. e23 (2014); M. C. Smith, R. Till & M. C. Smith, 51 Mol. Microbiol. 1719 (2004)). The three linker pairs attp$^{GG}$/attB$^{GG}$, attP$^{AC}$/attB$^{AC}$, and attP$^{CA}$/attB$^{CA}$ can therefore be selected as an orthogonal set. FIG. 60 shows an example using these orthogonal linker pairs.

Figure 64:
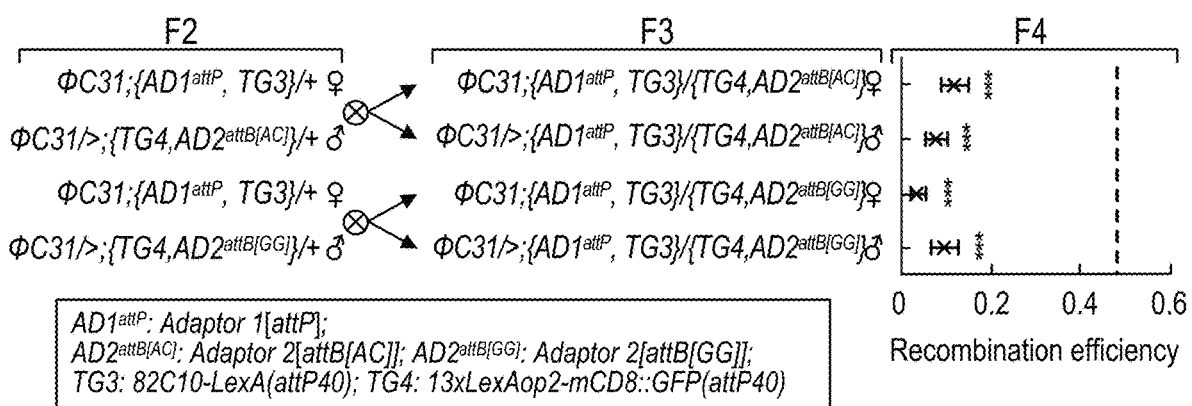
FIG. 64 is a plot showing the recombination efficiency between wild-type attP and mutated attB at genomic locus attP40. The error bars indicate the 95% confidence interval of the efficiency. The recombining efficiencies are compared to the average recombination efficiency of wild-type attP/attB linker in FIG. 23 (48%, dashed line) using a binomial test (***: P<10$^{-6}$).

To test the orthogonality among these mutated attP/attB sites, the transgenes with AD2 containing attB$^{GG}$ or attB$^{AC}$ site were created and crossed with the transgene with AD1 containing wild-type attP site (FIG. 64). As with the recombination induced by the wild-type attP/attB linker pair, the efficiency of the recombination in FIG. 64 is defined as the frequency of the progeny without fluorescent markers. The efficiencies in FIG. 64 were significantly lower than the average efficiency of wild-type attP/attB linker pair (48%, FIG. 23).

Figure 66:
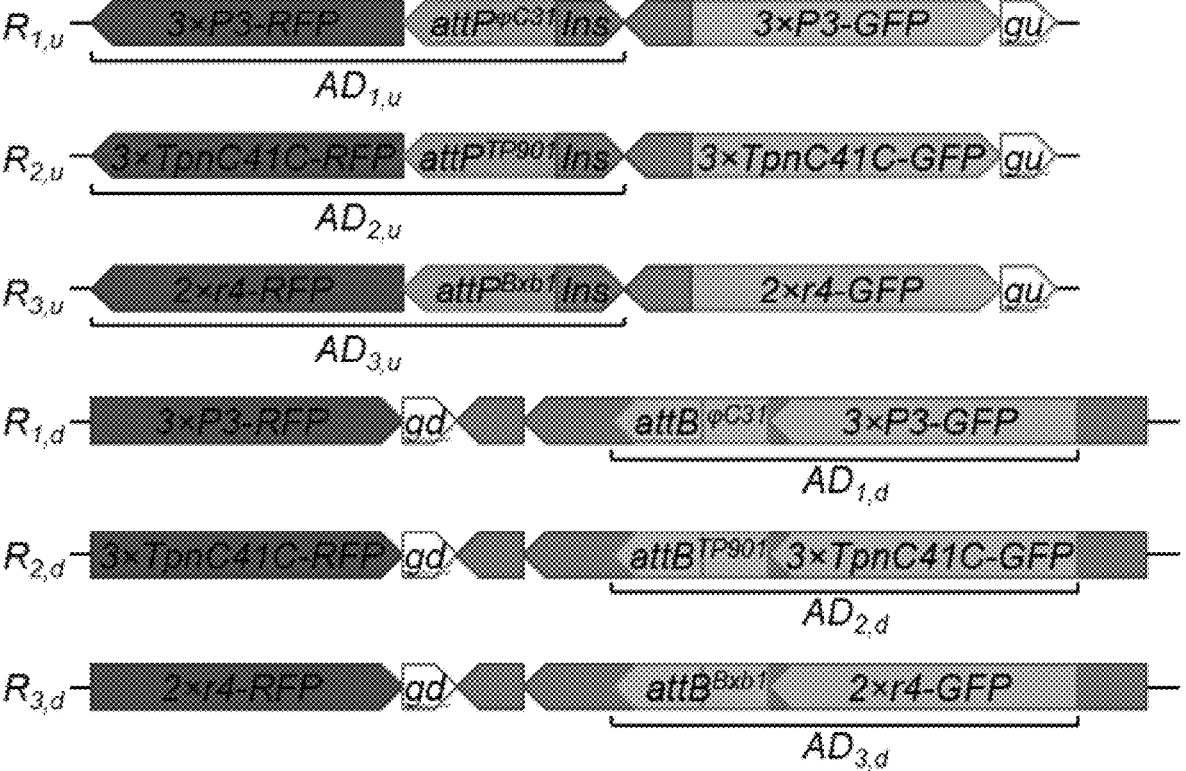
FIG. 66 is an example illustration of maps of recombinators following the designs in FIG. 46. This example uses three orthogonal attP/attB pairs corresponding to three unidirectional serine recombinase QC31, Bxb1, and TP901.

Another strategy used to design orthogonal attP/attB pairs involves using different unidirectional serine recombinase homologs. Examples of unidirectional serine recombinases include, without limitation, φBT1, Bxb1, φC31, TP901, R4, Wβ, A118, MR11, TG1, φRV1, φFC1, U153, and gp29 (K. Tomimatsu et al., 7 FEBS Open Bio. 306 (2017); M. C. Smith & H. M. Thorpe, 44 Mol. Microbiol. 299 (2002); Z. Xu & W. R. Brown, 16 BMC Biotechnol. 13 (2016)). These recombinases have different targeted recombination sites. Their orthogonality also has been well characterized by experiments (K. Tomatsu et al., 7 FEBS Open Bio. 306 (2017); A. P. Farrugio & M. P. Calos, 3 Biol. Open 895 (2014)). The efficiency of these recombinases varies in different species (Z. Xu & W. R. Brown, 16 BMC Biotechnol. 13 (2016); Z. Xu et al., 13 BMC Biotechnol. 87 (2013); R. Voutev & R. S. Mann, 62 Biotechniques 37 (2017); R. Voutev & R. S. Mann, 8 G3 (Bethesda) 1399 (2018); R. Voutev & R. S. Mann, 9 G3 (Bethesda) 983 (2019)), and tests and optimization can be used to adapt the recombinase system accordingly. FIG. 66 shows an example using the orthogonal attP/attB pairs corresponding to three unidirectional serine recombinase φC31, Bxb1, and TP901.

Example 7. Nuclease-Induced Adaptor Insertion

Figure 25:
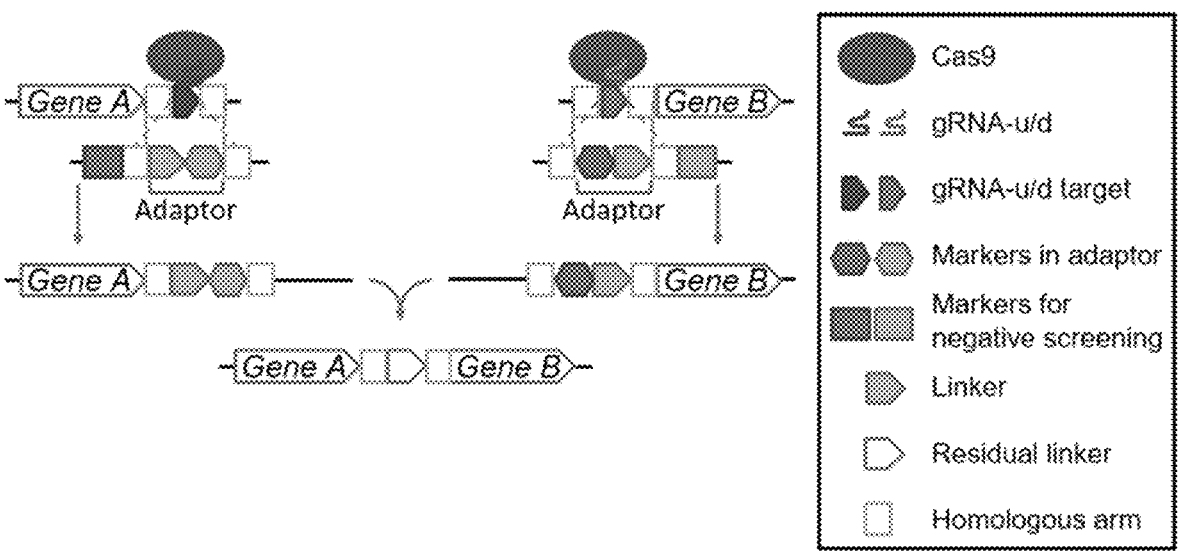
FIG. 25 is an illustration of a nuclease-induced adaptor insertion approach using a nuclease cut upstream or downstream of the existing transgene to insert the adaptor. After the recombination, the homologous arms and residual linker still exist between the recombined transgenes.

FIG. 25 illustrates a provided approach using a nuclease to induce a DNA cut upstream or downstream of the existing transgene to insert the adaptor. The nuclease (complex) can be, for example, Cas9/gRNA (M. Jinek et al., 337 Science 816 (2012); L. Cong et al., 339 Science 819 (2013)), TALEN (Transcription Activator-Like Effector Nucleases) (M. Christian et al., 186 Genetics 757 (2010)), or ZFN (Zink-Finger Nucleases) (M. Bibikova et al., 300 Science 764 (2003)). Some Cas9 variants can also be used to insert the adaptor, including CRISPEY and prime editor (E. Sharon et al., 175 Cell 544 (2018); A. V. Anzalone et al., 576 Nature 149 (2019)). The nuclease and the DNA template containing the adaptor can be injected, for example, into the germlines of the transgenic strain. The transgenic strain can also be crossed with a pre-engineered strain termed "recombinator" for the adaptor insertion.

The recombinator strain contains the following components: the adaptor flanked with the sequence homologous to the upstream or the downstream of the target transgene, the nuclease for DNA cutting, and a selective marker for negative screening (FIG. 25). In the F1 generation, the nuclease cuts the target transgene to induce homologous directed repair using the adaptor as a template. After the repair, the adaptor is inserted into the end of the target transgene, and the nuclease and the selective marker are dropped off. For the screening, the selective marker is used for negative screening, as it is orthogonal to the marker in the adaptor. The transgenic strain with the adaptor will generally only contain the marker in the adaptor, but not the marker for negative screening (FIG. 25). The nuclease-induced adaptor insertion strategy can be used to insert the adaptors with homologous linkers (FIG. 52) or attP/attB linkers (FIG. 57). The details of the two examples are described in Examples 5 and 6.

The recombination strategies described in Example 1 and Example 2 determine the number of markers necessary for the entire set of recombinators. The activation recombination strategy only needs one pair of adaptors. The minimum number of markers for the activation recombination strategy is two. The coordination recombination strategy requires at least three pairs of adaptors. The minimum number of markers for the coordination recombination strategy is six. Details of how to organize these markers are described in Example 8 and Example 9.

Figure 26:
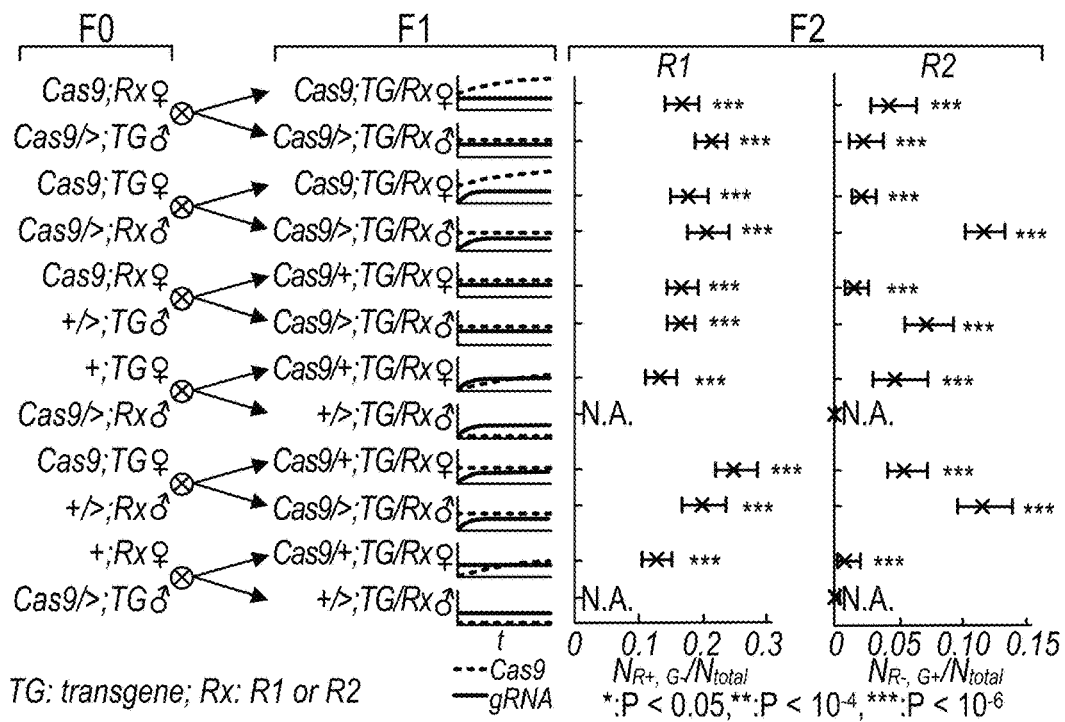
FIG. 26 presents experimental results demonstrating the efficiency of nuclease-induced adaptor insertion in *Drosophila*. The efficiency of nuclease-induced adaptor insertion is defined as the percentage of the desired animals among all progeny. Maternal Cas9 and gRNA expression can influence the efficiency of R1 and R2. The blue and purple curves show the expression level of gRNA and Cas9 in 12 possible cross designs. The error bars indicate the 95% confidence interval of the efficiency. The insertion efficiencies are compared to natural recombination using a binomial test (***: $P<10^{-6}$). The efficiency of R1 is ~15%. The efficiency of R2 is ~8%.
Figure 27:
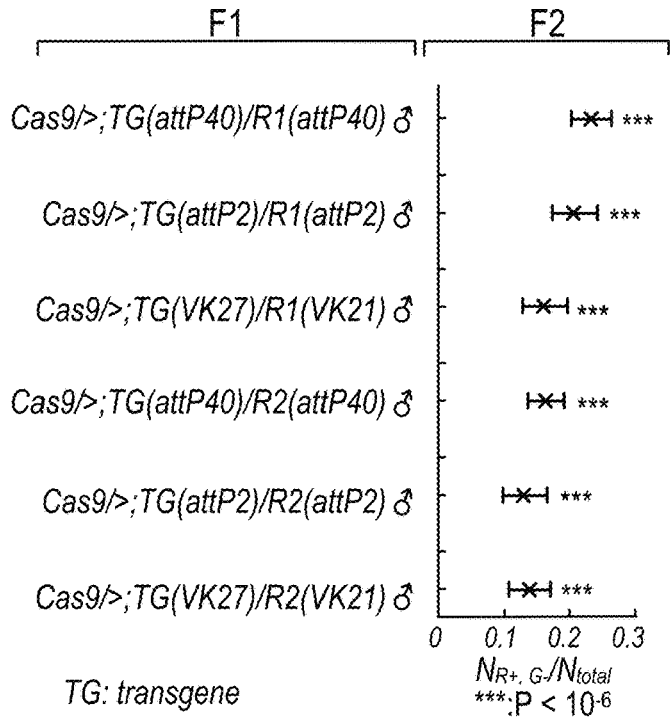
FIG. 27 presents experimental results demonstrating the efficiency of nuclease-induced adaptor insertion at different genomic loci in *Drosophila*. The efficiency of nuclease-induced adaptor insertion is defined as the percentage of the desired animals among all progeny. The error bars indicate the 95% confidence interval of the efficiency. The insertion efficiencies are compared to natural recombination using a binomial test (***: $P<10^{-6}$).

The insertion requires homologous sequences flanking the adaptor. In *Drosophila*, an approximately 1-kb homologous sequence and a well-functioning nuclease can be used together to reach around 10% insertion efficiency, as demonstrated by the data of FIGS. 26 and 27. The insertion efficiency is defined here as the fraction of organisms containing the transgene with the adaptor in all F2 offspring.

The adaptor insertion site can be vector-specific or locus-specific (FIGS. 28 and 29). In the vector-specific strategy, illustrated in FIG. 28, the homologous sequence flanking the adaptor matches a common sequence on the vector engineered for transgenic organism generation. This strategy allows the insertion of the adaptor into any transgenic strain using the same vector backbone. It also allows disruption of the marker in the transgenic backbone by inserting an adaptor into it, avoiding the accumulation of the markers in the resulting transgenic tandem. In the locus-specific strategy, illustrated in FIG. 29, the sequence around the transgenic docking site is used as the homologous sequence flanking the adaptor. This strategy inserts the adaptor to all transgenes docking on the same locus, and can be particularly suitable with some model organisms like mice, where the transgenes usually do not contain the vector backbone.

Example 8. Marker Organization in the Recombinators for the Activation Recombination Strategy The activation recombination strategy only needs one pair of adaptors (AD1 and AD2). In this case, we only need one pair of recombinators (R1 and R2) to insert the pair of adaptors. To design the markers in R1 and R2, the cross diagram for the adaptor insertion is first constructed as in FIG. 31. As shown in the cross diagram, the transgene first crosses with R1 or R2 to form a transheterozygote. Then, the transheterozygote crosses with a wild-type or balancer strain. The progeny of this cross contains transgene with an adaptor, original transgene, and original R1 or R2. To distinguish the transgene with an adaptor from other undesired strains, additional markers in R1 and $R^2$ are designed following the equations of FIG. 32:

$$\{M_{TG}\} \cup \{M_1\} \neq \{M_{TG}\};$$

$$\{M_{TG}\} \cup \{M_1\} \neq \{M_1\} \cup \{M_{R1}\};$$

$$\{M_{TG}\} \cup \{M_2\} \neq \{M_{TG}\}; \text{ and}$$

$$\{M_{TG}\} \cup \{M_2\} \neq \{M_{R2}\} \cup \{M_2\};$$

where $M_1$ and $M_2$ are the markers in AD1 and AD2, and $M_{R1}$ and $M_{R2}$ are the negative-screening markers in R1 and R2. $M_{TG}$ is the marker in the transgene.

Two factors complicate the influence of $M_{TG}$ on the selection of $M_{R1}$ and $M_{R2}$. First, $M_{TG}$ provides additional information for distinguishing. Second, $M_{TG}$ may be disrupted by adaptor insertion. If $M_{TG}$ is made use of in the selection (letting $\{M_{TG}\} \neq \emptyset$), the constraints on markers can be simplified as shown in FIG. 33, with:

$$M_1 \neq M_{TG}, \ M_{R1} \neq M_{TG}$$

$$M_2 \neq M_{TG}, \ M_{R2} \neq M_{TG}$$

If $M_{TG}$ is ignored or $M_{TG}$ is difficult to observe in the selection (letting $\{M_{TG}\} = \emptyset$), the constraints on markers can be simplified as shown in FIG. 33, with:

$$M_1 \neq M_{R1}$$

$$M_2 \neq M_{R2}$$

Figures 30, 31:
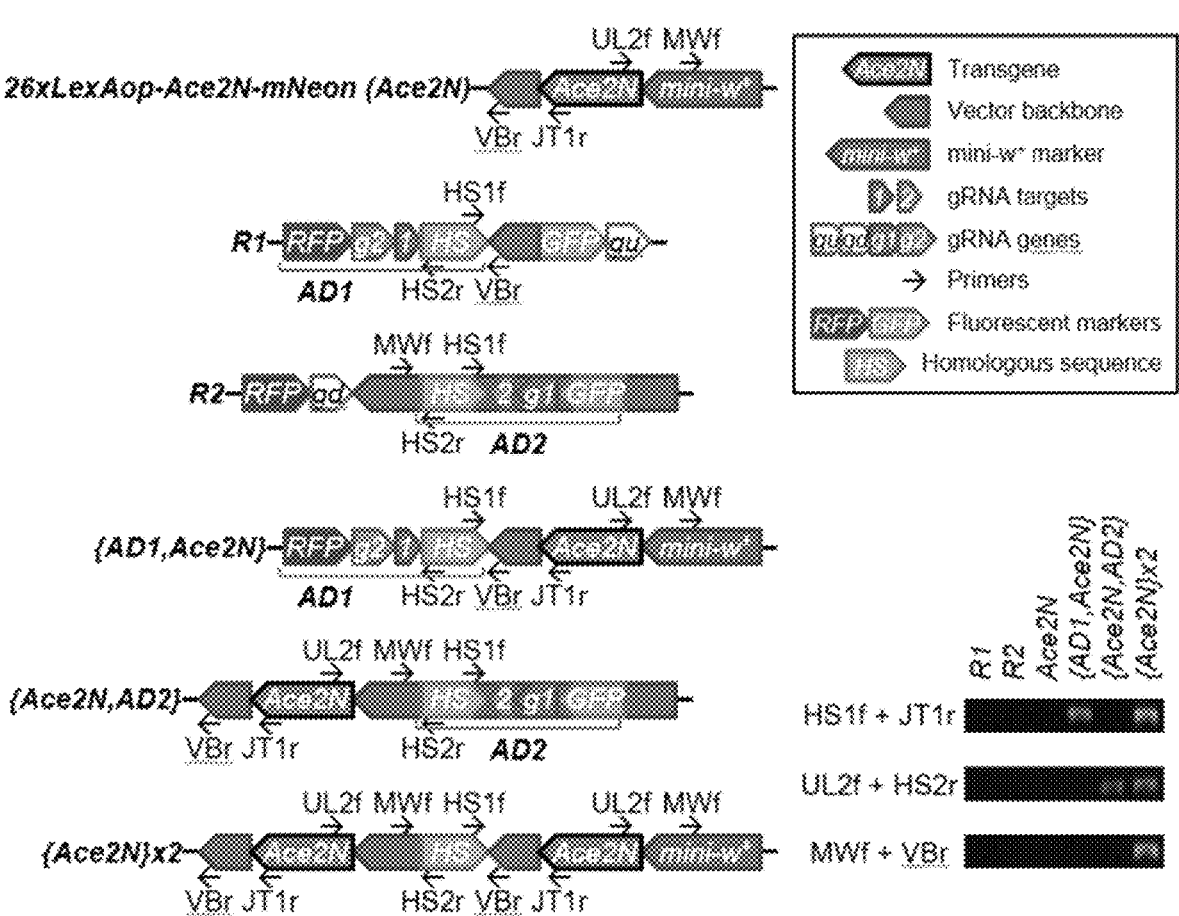
FIG. 30 provides experimental results demonstrating the typing of recombination products by PCR. To confirm that strains screened by fluorescent markers are inserted or recombined correctly, PCR can be used to verify the strains in all steps. The purpose of the recombination depicted is to duplicate the copy number of a transgene fluorescent voltage indicator (Ace2N). In this recombination, Gene A and Gene B are both Ace2N. The arrows in the left panel indicate the directions and binding sites of primers. For example, HS1f is designed on AD1 and JT1r on Ace2N. The Ace2N with AD1 insertion shows a PCR band. The original Ace2N transgene and R1 only have one of the primer pairs binding to them, and thus does not show a band in the PCR results. The Ace2N with AD2 and the duplication of Ace2N are similarly confirmed to be correct.
FIG. 31 presents a diagram of the marker genotype in one step of recombination, showing the orthogonality of markers in the adaptors and recombinators used in the activation recombination strategy. The transgene is first crossed with Recombinator 1 or 2 (($M_1$,$M_{R1}$) or ($M_{R2}$,$M_2$)); and then the transheterozygote was crossed with a wild-type strain (or a balancer strain). In the last generation, the transgene with an adaptor is selected. Undesired genotypes are shown in gray.

In the example depicted in FIG. 30, $M_{TG}$ is mini-w$^+$ (red eye). To simplify the design of R1 and R2, fluorescent markers are used for $M_1$, $M_2$, $M_{R1}$, and $M_{R2}$ to avoid mini-w$^+$ from conflicting with them, but mini-w$^+$ is not relied on for genotype selection. Therefore, at least two orthogonal markers are necessary. In this example, 3×P3-DsRed are used as $M_1$ and $M_{R2}$; and 3×P3-GFP are used as $M_2$ and $M_{R1}$.

Example 9. Marker Organization in the Recombinators for the Coordination Recombination Strategy The coordination recombination strategy requires three pairs of adaptors ($AD_{i,u}$ and $AD_{i,d}$, i=1, 2, or 3), where $AD_{i,u}$ and $AD_{i,d}$ represent the upstream and downstream adaptor in adaptor pair i. This strategy requires three pairs of recombinators ($R_{i,u}$ and $R_{i,d}$, i=1, 2, or 3) to insert the corresponding adaptors. FIG. 34 shows the cross diagram for inserting the upstream and downstream adaptors. As outlined in this diagram, TG (the transgene) is first crossed with $R_{i,u}$ in a first step. Second, TG/$R_{i,u}$ (the transheterozygote of the transgene and $R_{i,u}$) is crossed with $R_{j,d}$ (j≠i). Third, $\{AD_{i,u},TG\}/R_{j,d}$ (the transheterozygote of $R_{j,d}$ and the transgene with $AD_{i,u}$) is selected and crossed with wild-type or balancer strain. Fourth, $\{AD_{i,u},TG,AD_{j,d}\}$ (the transgene with $AD_{i,u}$ and $AD_{j,d}$) is selected. The two steps of selection in steps three and four require the markers to satisfy the following equations of FIG. 35:

$$\{M_{i,u}\} \cup \{M_{TG}\} \cup \{M_{j,Rd}\} \cup \{M_{j,d}\} \neq \{M_{TG}\} \cup \{M_{j,Rd}\} \cup \{M_{j,d}\}$$

$$\{M_{i,u}\} \cup \{M_{TG}\} \cup \{M_{j,Rd}\} \cup \{M_{j,d}\} \neq \{M_{i,u}\} \cup \{M_{i,Ru}\} \cup \{M_{j,Rd}\} \cup \{M_{j,d}\}$$

$$\{M_{i,u}\} \cup \{M_{TG}\} \cup \{M_{j,d}\} \neq \{M_{i,u}\} \cup \{M_{TG}\}$$

$$\{M_{i,u}\} \cup \{M_{TG}\} \cup \{M_{j,d}\} \neq \{M_{j,Rd}\} \cup \{M_{j,d}\}$$

Whether the genotype selection relies on the marker in the transgene affects the choice of markers in adaptors and recombinators. In the two cases, the constraints on markers can be simplified as that shown in FIGS. 36-39. For reasons similar to those discussed in Example 8, it is preferable not to use the marker in the transgene for genotype selection.

Figure 40:
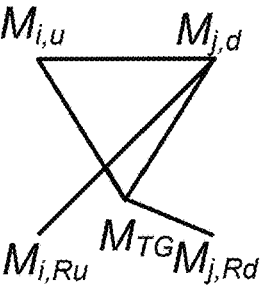
FIG. 40 presents a graph showing the orthogonality of the markers in the adaptors and recombinators of FIGS. 34 and 35 if the order of adding the upstream and downstream adaptor is switched and the marker in the transgene is used for distinguishing.
Figure 41:
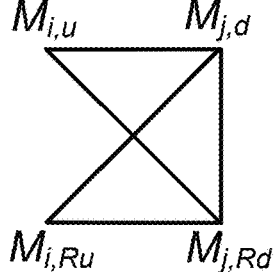
FIG. 41 presents a graph showing the orthogonality of the markers in the adaptors and recombinators of FIGS. 34 and 35 if the order of adding the upstream and downstream adaptor is switched and the marker in the transgene is not used for distinguishing.
Figure 42:
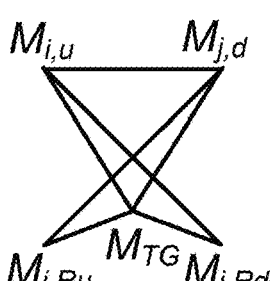
FIG. 42 presents a graph showing the orthogonality of the markers in the adaptors and recombinators of FIGS. 34 and 35. The orthogonality supports the addition of the upstream and downstream adaptor in both orders if the marker in the transgene is used for distinguishing.

In the cross diagram of FIG. 34, the upstream adaptor is added first, followed by the downstream adaptor. If adding of the downstream adaptor first before the upstream adaptor is also allowed, $M_{i,u}$ can be interchanged with $M_{i,d}$, and $M_{i,Ru}$ can be interchanged with $M_{i,Rd}$ in FIGS. 37 and 39. The symmetric graphs in FIGS. 40 and 41 are then merged with the graphs in FIGS. 37 and 39 to create the graphs in FIGS. 42 and 43. Therefore, these graphs show the orthogonality constraints for markers supporting the addition of the upstream adaptor and the downstream adaptor in both orders.

The markers in upstream and downstream adaptors preferably also support the recombination steps in the coordination recombination strategy. Thus, the markers $M_{i,u}$ and $M_{j,d}$ should follow the graph in FIG. 11. Here, $M_{i+2^{\wedge}\{k-1\}+1,u}$ and $M_{i+2^{\wedge}\{k-1\},d}$ in FIG. 11 are not merged to simplify into the graph in FIG. 12 because FIG. 43 requires $M_{i,u} \neq M_{j,d}$. Rather, $M_{m+3n,x}$ can be merged into $M_{m,x}$ (m=1, 2, or 3; n=0, 1, 2, 3, . . . ; x=u or d). This merging does not violate the constraints on $M_{i+1,u} \neq M_{i+2^{\wedge}\{k-1\}+1,u}$ and $M_{i+2^{\wedge}\{k-1\},d} \neq M_{i+2^{\wedge}k,d}$ because $i+1 \not\equiv i+2^{k-1}+1 \pmod{3}$ and $i+2^{k-1} \not\equiv i+2^k \pmod{3}$. Considering each of the three cases for i (i=0, 1, or 2 (mod 3)) and the two cases of $2^k$ ($2^k \equiv -1$, or 1 (mod 3)), all six cases of the graphs can be drawn (FIG. 44) and merged into one graph containing $M_{m,x}$ (m=1, 2, or 3; x=u or d) (FIG. 45).

Figure 43:
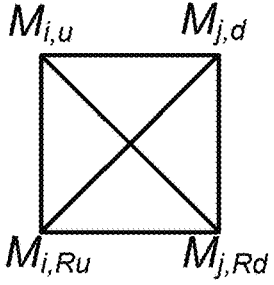
FIG. 43 presents a graph showing the orthogonality of the markers in the adaptors and recombinators of FIGS. 34 and 35. The orthogonality supports the addition of the upstream and downstream adaptor in both orders if the marker in the transgene is not used for distinguishing.
Figure 44:
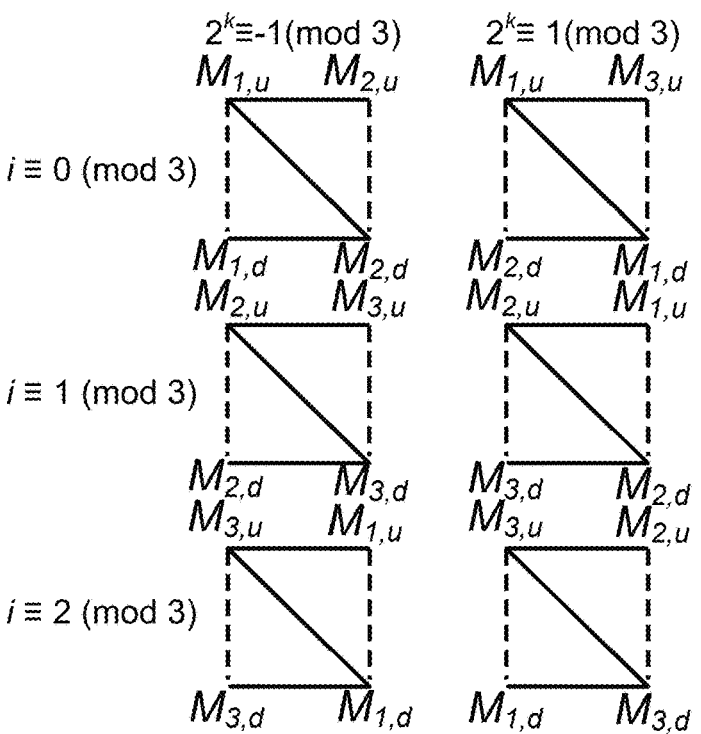
FIG. 44 presents all six possible module graphs describing the orthogonality of markers in adaptors for the coordination recombination strategy.
Figure 45:
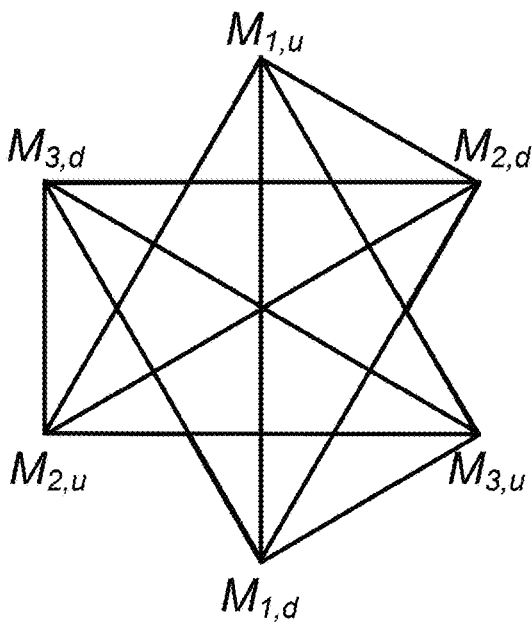
FIG. 45 presents a combination of the six modular graphs in FIG. 44 to form a graph of all the markers in adaptors.
Figure 46:
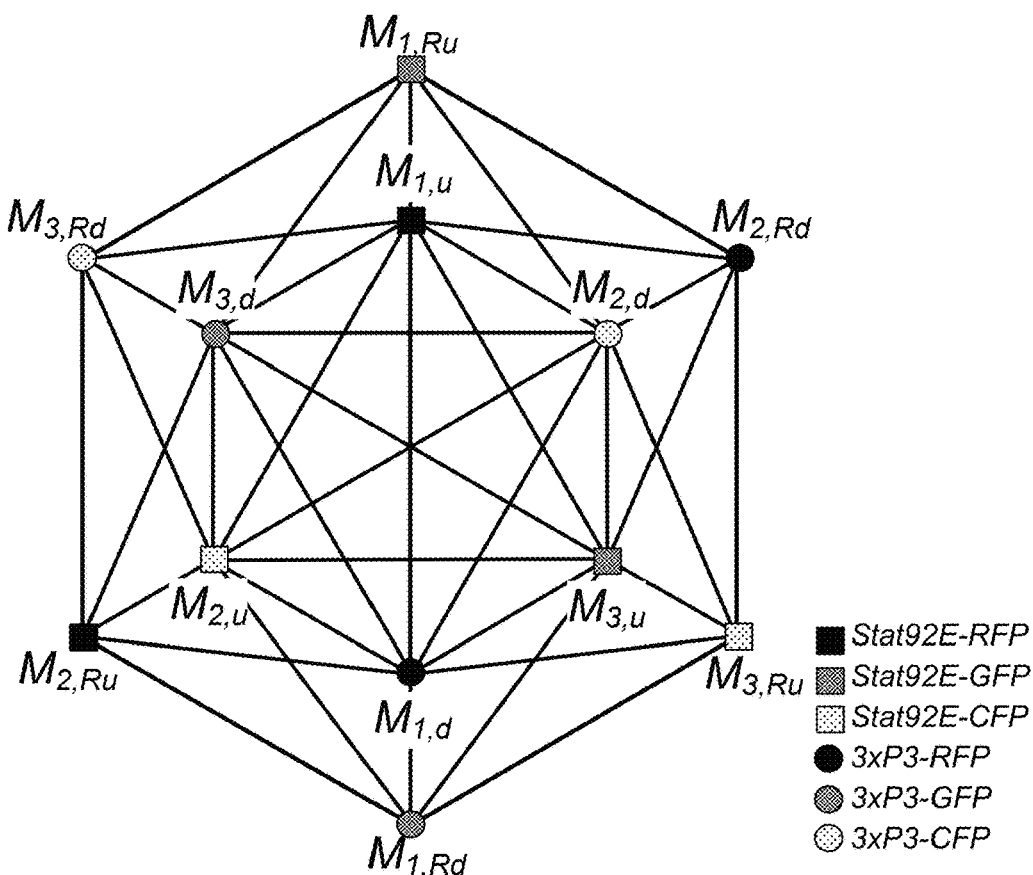
FIG. 46 presents a graph of markers in adaptors and recombinators for the coordination recombination strategy. The color cycles and squares indicate one acceptable labeling pattern of the graph.

Because markers used in the coordination recombination strategy should follow the previously discussed constraints in the adaptor insertion steps and recombination steps, the graphs in FIGS. 43 and 45 are combined to create the graph in FIG. 46. The 6 nodes $M_{m,x}$ (m=1, 2, or 3; x=u or d) in the center of this diagram are fully connected. Thus, labeling this diagram requires at least six orthogonal markers. In FIG. 46, the red, green, and cyan cycles and squares show one acceptable labeling pattern of the graph. Accordingly, six orthogonal markers are sufficient for the coordination recombination strategy. FIGS. 60 and 66 show two examples of recombinators satisfying the constraints on orthogonal markers in FIG. 46.

Two promoters whose expression patterns are orthogonal to the 3×P3 promoter were synthesized and tested. The TpnC41C promoter drives expression in the insect tubular muscles in the thorax (M. B. Chechenova, S. Maes, & R. M. Cripps, 10 PLoS One e0144615 (2015)); and the r4 promoter drives expression in the insect adipose tissue (W. An & P. C. Wensink, 9 Genes & Development 256 (1995)). To reduce the length and increase the expression level of the two promoters, multiple copies of the transcriptional factor binding sites of the two promoters were synthesized. The sequence of the 3×TpnC41C promoter is:

```
                                        (SEQ ID NO: 1)
ttcacaaataccatttCCctaaaaataaCCttcacaaataccatttCCcta aaaataaCCttcacaaataccatttCCctaaaaataa
```

The sequence of the 2×r4 promoter is:

```
                                        (SEQ ID NO: 2)
TTAAAATAATCAGGCGTAGATTAAAATAATCAGGCGGTCATTAAAATAATC

AGGCGGAGATTAAAATAATCAGGCGatgcatTTAAAATAATCAGGCGTAGA

TTAAAATAATCAGGCGGTCATTAAAATAATCAGGCGGAGATTAAAATAATC

AGGCG
```

Figure 65:
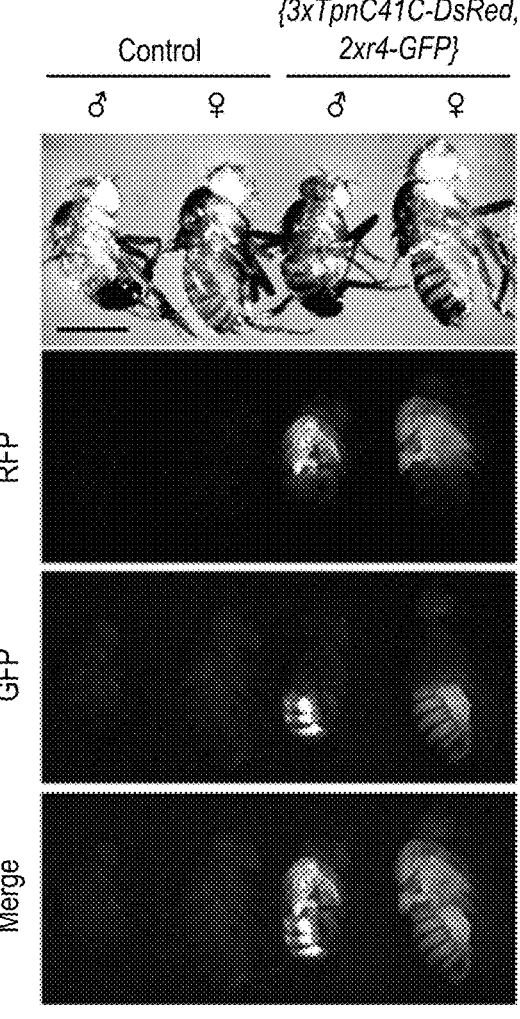
FIG. 65 shows the expression patterns of promoter 3×TpnC41C and 2×r4. The 3×TpnC41C promoter drives the RFP expression in the insect tubular muscles in the thorax. The 2×r4 promoter drives GFP expression in the insect adipose tissue in the abdomen. The expression patterns driven by the two promoters are orthogonal. The sex of the fly does not influence the expression pattern of the two promoters.

A transgenic fly strain {3×TpnC41C-DsRed, 2×r4-GFP} was created and used to confirm the two designed promoters are orthogonal (FIG. 65).

Example 10. CRISPR-Transposase-Induced Adaptor Insertion

Figure 47:
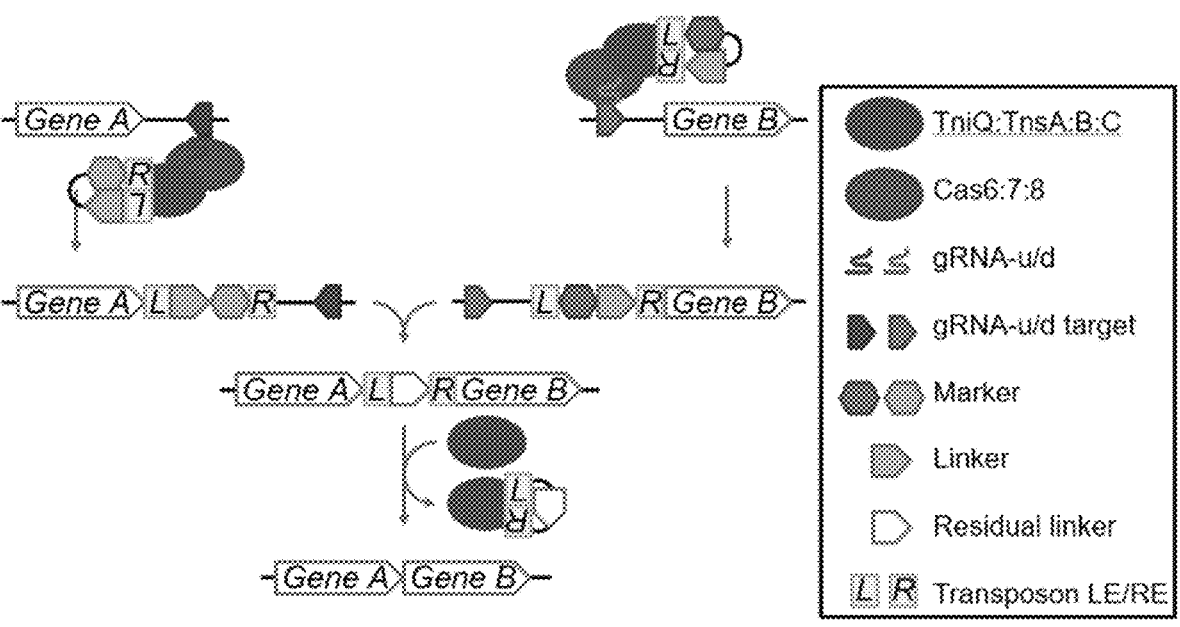
FIG. 47 is an illustration of Cas9-transposase-induced adaptor insertion. The gRNA target with the correct direction permits the adaptor to be inserted between the transgene and the gRNA target. In this case, the gRNA target can be dropped off after the recombination induced by the adaptor. After the recombination, the transposase can also be used to remove the residue sequence of the adaptor.

Similar to the Nuclease-induced insertion approach of Example 7, the CRISPR-transposase-induced insertion approach also inserts the adaptor into the upstream or the downstream of the transgene. In this design, as shown in FIGS. 47, 52, and 53, the CRISPR transposase (S. E. Klompe et al., 571 Nature 219 (2019); J. Strecker et al., 365 Science 48 (2019)) is used instead of nuclease. Correspondingly, the transposon sequence is used to replace the homologous sequence flanking the adaptor.

The CRISPR transposase induces the transposon insertion into approximately 60 bp downstream of the gRNA target sequence (S. E. Klompe et al., 571 Nature 219 (2019); J. Strecker et al., 365 Science 48 (2019)). Thus, the gRNA target sequences (the red and blue pentagon in FIG. 47) typically point to the transgene to be recombined to make the transgene at their downstream. Then, the CRISPR transposase inserts the adaptor between the transgene and the gRNA target. In this case, the gRNA target sequences can be dropped off after the recombination induced by the adaptor. After the recombination, the transposase is used to remove the residual sequence of the adaptor. Here this transposon excision requires both transposon left and right elements (yellow rectangles in FIG. 47). Therefore, the transposon containing the two adaptors is in the same orientation. The two gRNA target sequences, however, are in opposite orientations. Some CRISPR transposases insert the transposon only in the same orientation as the gRNA target sequence (J. Strecker et al., 365 Science 48 (2019)), and some insert the transposon in either the same or the opposite orientations as the gRNA target sequences (S. E. Klompe et al., 571 Nature 219 (2019)). Only the CRISPR transposase inserting the transposase in either orientation can support the transposon excision after the recombination.

CRISPR-transposase-induced insertion can reduce the length of the residual sequence to less than 100 bp (FIG. 47), as compared to the approximately 3 kbp residual sequence between the two recombined genes in the nuclease-induced insertion depicted in FIG. 25. Because of the imprecise insertion and excision, additional quality control is required to ensure the sequence between the recombined transgenes does not influence the transgenes' function. The design of selective markers for negative screening is similar to that in the nuclease-induced insertion approach (Example 7). The adaptor insertion site can be either vector-specific or locus-specific, as in the nuclease-induced insertion approach (Example 7).

Example 11. Directed Synthesis or Cloning Adaptors

Figure 61:
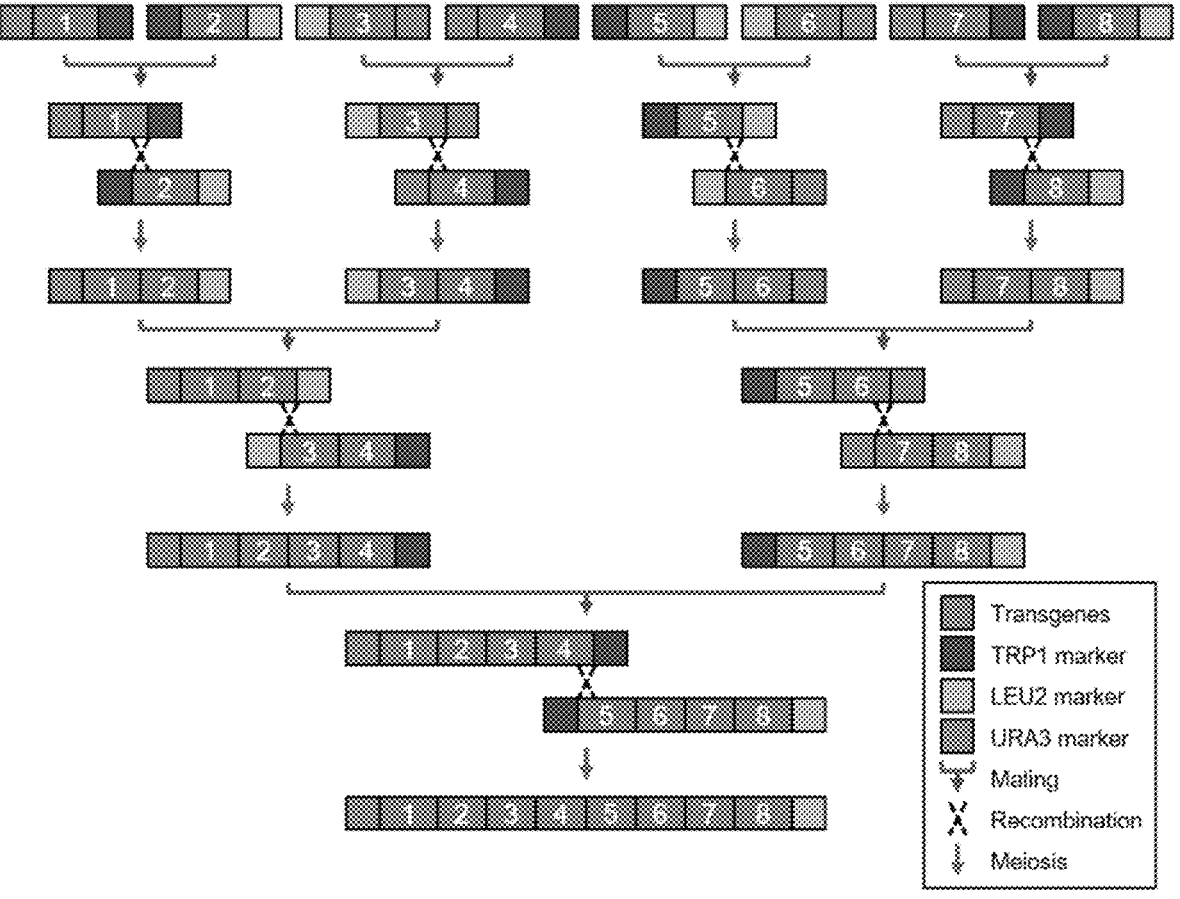
FIG. 61 is an illustration of the recombination of multiple transgenes in yeast with an approach using directly synthesized adaptors and the coordination recombination strategy.

The adaptor in the transgene can alternatively be directly synthesized or cloned when making the constructs. Because synthesizing adaptors in the transgenes does not require recombinators for adaptor insertion, this approach is suitable for use with the coordination recombination strategy, rather than with the activation recombination strategy. This design can be used, for example, to assemble a large transgenic tandem without any unwanted residual sequence between transgenes. In this example shown in FIG. 61, the large transgenic tandem to be constructed is divided into several transgenic fragments with approximately 1 kb overlaps on the upstream and downstream ends. These overlaps work as the homologous linkers for recombination (FIG. 61). This design beneficially can avoid producing repeat sequences of the residual linkers and ensure the linkers are orthogonal. The order of these transgenes, however, cannot be freely changed in the recombination processes. The design of the markers follows the constraints described in Example 4. The minimum number of orthogonal markers is 3 (FIG. 61).

Besides the homologous linkers, the attP/attB linkers can also be directly synthesized or cloned into the transgenes in the beginning. As mentioned in Example 3 and 4, the minimum number of orthogonal linkers and markers is 3 in this design. After the recombination, an attR site is left between the two recombined transgenes or transgenic tandems. Although using the attP/attB linker cannot completely avoid the residual sequence after recombination. The residual sequence is less than 100 bp long, which is much shorter than the nuclease-induced adaptors insertion approach. The attP/attB linkers provide some flexibility to adjust the orders of the transgenes. If two transgenes have the same attP/attB linkers, they are interchangeable.

Figure 48:
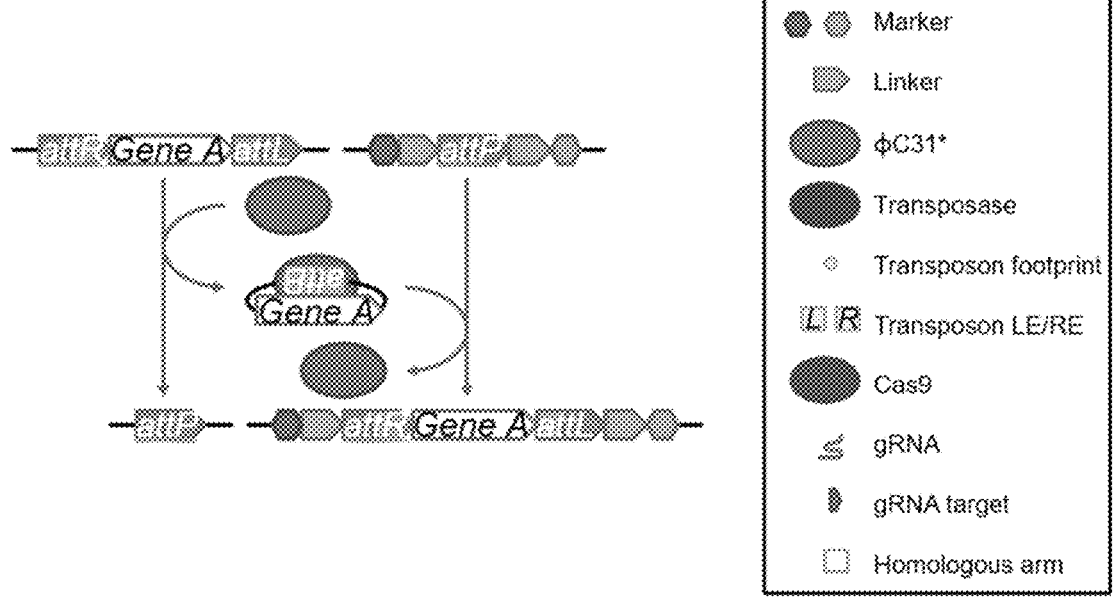
FIG. 48 is an illustration of the addition of an adaptor to a transgene via translocation of the transgene by φC31*.
Figure 49:
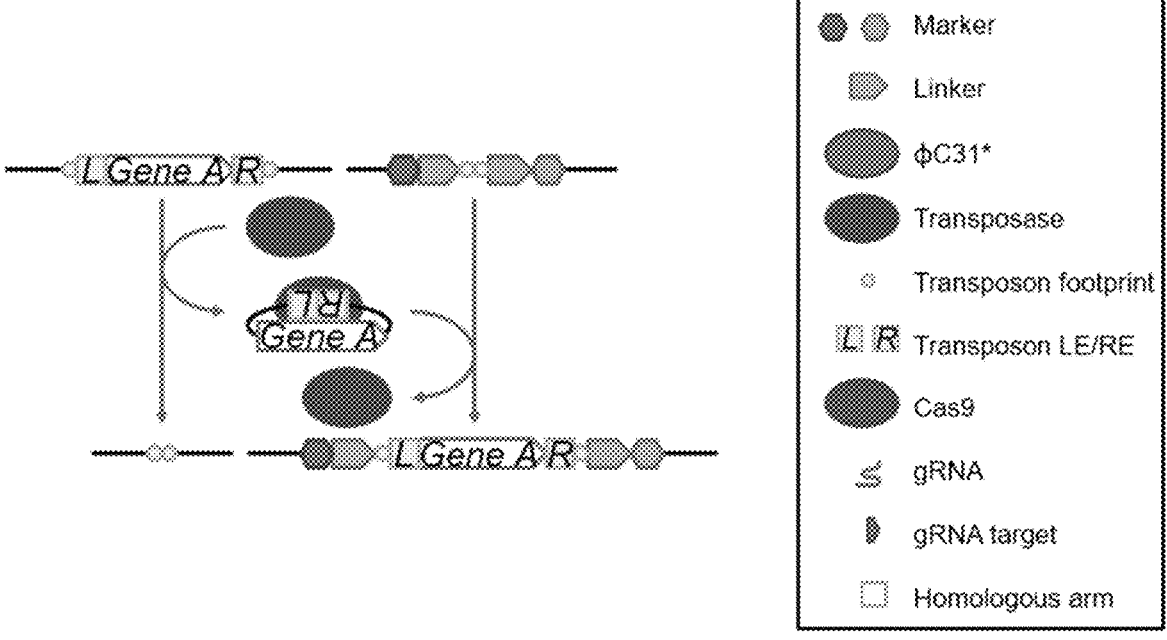
FIG. 49 is an illustration of the addition of an adaptor to a transgene via translocation of the transgene by the transposase.
Figure 50:
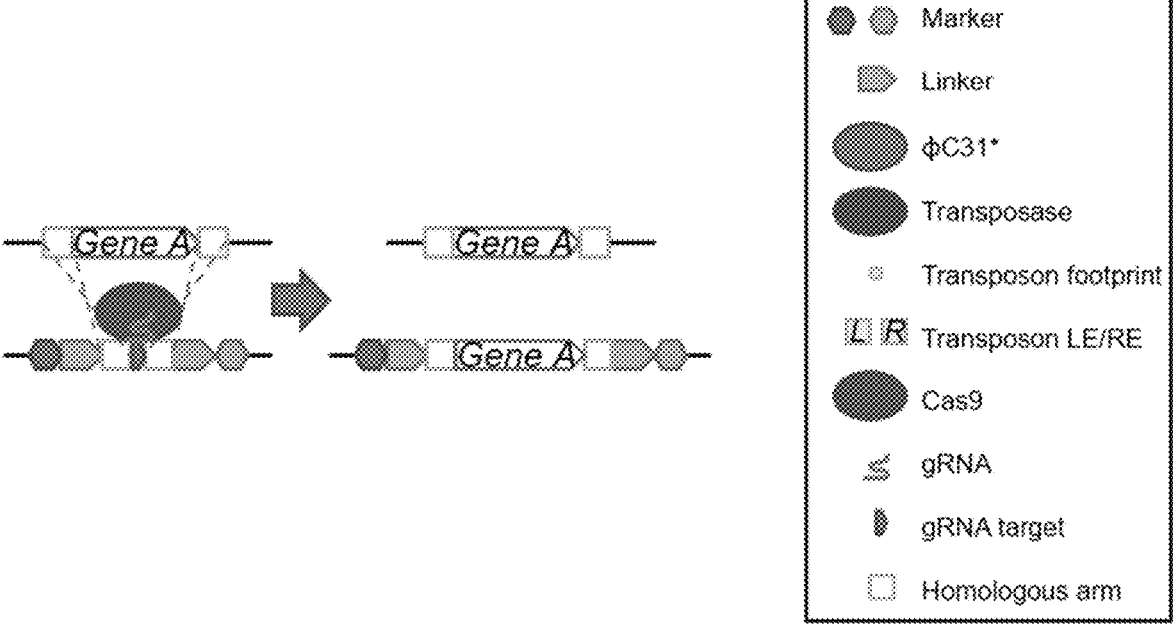
FIG. 50 is an illustration of adding an adaptor to a transgene via duplicating the transgene into the adaptor nest.

Example 12. Adding an Adaptor by Translocation or Duplication of the Existing Transgene Empty transgenic strains can also be created with adaptors called "nest strains," and then the transgene targeted for recombination can be translocated or duplicated to the nest strain. A plasmid can also be injected into the nest strain to make the transgene with adaptors, as shown in FIGS. 48-50.

The procedure used to translocate the transgene for recombination into the nest strain depends on the approaches for making the original transgene. If the original transgenes are made by the attP/attB system, they can be translocated by φC31 and φC31* (J. M. Knapp, P. Chung & J. H. Simpson, 199 Genetics 919 (2015)). In this case, the nest strain preferably contains an attP site to dock the original transgene, as shown in FIG. 48. If the original transgene is made by the transposase, it can be translocated by the same transposase. In this case, the nest strain preferably contains a transposon footprint to dock the original transgene, as shown in FIG. 49. The site-specificity of the φC31 is much higher than that of the transposase. Thus, the transgenes made by the attP/attB system have a higher chance of being translocated to the target rather than other random sites in the nest strain. Translocation is not sensitive to the distance of the original transgene and the nest transgene. Duplication of the transgene can be induced by nuclease cutting on the nest strain, as shown in FIG. 50. Here, the nest strain preferably contains the homologous arms fit for the backbone of the original transgene. Compared to the translocation, duplication induced by nuclease is more sensitive to the distance of the original transgene and the nest transgene.

Figure 51:
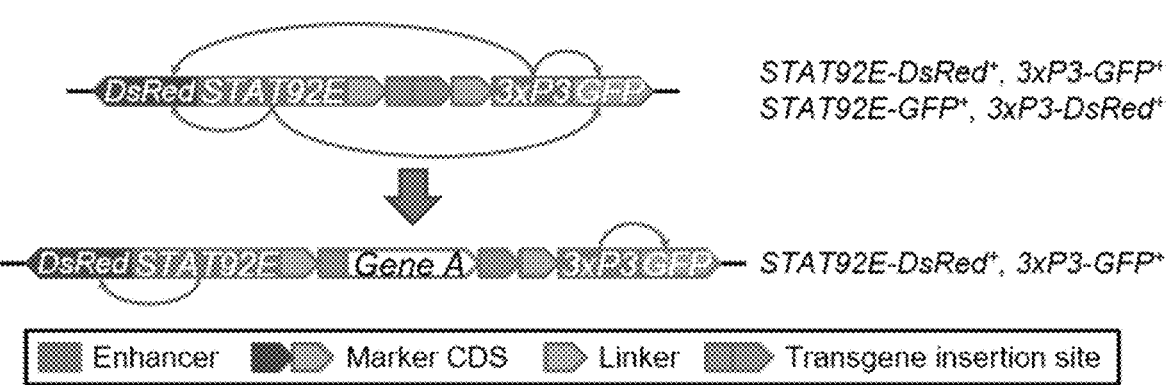
FIG. 51 is an illustration of the marker design for detecting a transgene translocated into a nest strain. In the nest strain, the total length of the linkers and the transgene insertion site is short. Thus, the 3×P3 enhancer is not far away from DsRed, CDS to drive DsRed expression. For the same reason, the STAT92E enhancer can also drive GFP expression. After the transgene (Gene A) insertion, the distance between 3×P3 and DsRed, and the distance between STAT92E and GFP are significantly increased. Therefore, 3×P3-DsRed$^+$ and STAT92E-GFP$^+$ phenotypes are not observable in the insertion strain.

FIG. 51 shows the special screening strategies to distinguish the transgene with adaptors from the original transgene and the empty nest transgene, special screening strategies are designed as shown in FIG. 51. Because the attP site or the transposon footprint is very short, the enhancers of the markers on the two adaptors can crosstalk in the empty nest strain (FIG. 51). The inserted transgene between the two adaptors, will push the two adaptors away from each other. As a result, the insertion breaks the crosstalk between the enhancers of the markers (FIG. 51). By observing the change of marker expression pattern, the transgenes with the two adaptors can be picked (FIG. 51). However, when using the nuclease-induced duplication to insert the transgene into the nest strain, the length of the homologous arms for duplicating the original transgene is long, and the two enhancers of the markers in the two adaptors may not crosstalk. In this case, PCR can be used to type the transgene with the two adaptors.

---

What is claimed is:

1. A method of creating a nucleotide sequence containing two or more transgenes or other nucleotide sequence fragments, the method comprising:

(a) providing 3 adaptor sequence pairs and i transgenes or other nucleotide sequence fragments, wherein i is an integer greater than 2;

(b) inserting (1) a first adaptor sequence of adaptor sequence pair 1 downstream of each transgene or other nucleotide sequence fragment x, and (2) a second adaptor sequence of adaptor sequence pair 3 upstream of each transgene or other nucleotide sequence fragment x, wherein $1 \leq x \leq i$, and wherein x−1 is divisible by 3;

(c) inserting (1) a first adaptor sequence of adaptor sequence pair 2 downstream of each transgene or other nucleotide sequence fragment y, and (2) a second adaptor sequence of adaptor sequence pair 1 upstream of each transgene or other nucleotide sequence fragment y, wherein $2 \leq y \leq i$, and wherein y−2 is divisible by 3;

(d) inserting (1) a first adaptor sequence of adaptor sequence pair 3 downstream of each transgene or other nucleotide sequence fragment z, and (2) a second adaptor sequence of adaptor sequence pair 2 upstream of each transgene or other nucleotide sequence fragment z, wherein $3 \leq z \leq i$, and wherein z−3 is divisible by 3;

(e) facilitating recombination between (1) a first matching linker sequence within each of the first adaptor sequence and the second adaptor sequence of adaptor sequence pair 1; (2) a second matching linker sequence within each of the first adaptor sequence and the second adaptor sequence of adaptor sequence pair 2; and (3) a third matching linker sequence within each of the first adaptor sequence and the second adaptor sequence of adaptor sequence pair 3; and (f) screening for correct recombination products using markers within each of the adaptor sequences.

2. The method of claim 1, wherein steps (b), (c), and (d) are performed in parallel.

3. The method of claim 1, wherein steps (b), (c), and (d) are performed using direct synthesis or cloning.

4. The method of claim 1, wherein steps (b), (c), and (d) are performed using enzyme-induced nucleotide sequence insertion or translocation.

5. The method of claim 4, wherein steps (b), (c), and (d) are performed using CRISPR/Cas9 or a variant thereof.

6. The method of claim 1, wherein step (e) is performed using natural recombination.

7. The method of claim 1, wherein step (e) is performed using enzyme-induced recombination.

8. The method of claim 7, wherein step (e) is performed using CRISPR/Cas9, φC31, or a variant thereof.

9. The method of claim 1, wherein step (f) is performed using negative screening.

10. The method of claim 1, wherein step (f) is performed using positive screening.

11. The method of claim 1, wherein the recombination produces an array of the transgenes or other nucleotide sequence fragments at the same genomic locus on a single chromosome.

12. The method of claim 11, wherein the single chromosome is a chromosome of a multicellular organism.

13. The method of claim 1, wherein the method further comprises, after the recombination, removing the markers within the adaptor sequences.

14. The method of claim 1, wherein the recombination is unidirectional recombination.

15. The method of claim 1, wherein the inserting of the adaptor sequences is locus specific.

16. The method of claim 1, wherein the first, second, and third matching linker sequences are orthogonal to one another.

17. The method of claim 16, wherein the first, second, and third matching linker sequences are an engineered set of orthogonal attP/attB pairs.

18. The method of claim 1, wherein creating the nucleotide sequence containing two or more transgenes or other nucleotide sequence fragments requires a number of recombination steps no more than the smallest integer greater than or equal to $\log_2(i)$.

19. The method of claim 1, wherein the markers comprise one or more fluorescence genes, one or more antibiotic resistance genes, one or more amino acid metabolism genes, or a combination thereof.

20. The method of claim 19, wherein the markers comprise one or more fluorescence genes.

* * * * *